United States Patent
Schulze et al.

(10) Patent No.: US 10,985,326 B2
(45) Date of Patent: Apr. 20, 2021

(54) COMPOUNDS COMPRISING TRIAZINE GROUP, FLUORENE-GROUP AND ARYL GROUP

(71) Applicant: NOVALED GMBH, Dresden (DE)

(72) Inventors: Benjamin Schulze, Dresden (DE); Regina Luschtinetz, Dresden (DE); Domagoj Pavicic, Dresden (DE)

(73) Assignee: Novaled GmbH, Dresden (DE)

( * ) Notice: Subject to any disclaimer, the term of this patent is extended or adjusted under 35 U.S.C. 154(b) by 77 days.

(21) Appl. No.: 16/183,856

(22) Filed: Nov. 8, 2018

(65) Prior Publication Data

US 2019/0140186 A1 May 9, 2019

(30) Foreign Application Priority Data

Nov. 9, 2017 (EP) .................................... 17200890

(51) Int. Cl.
*H01L 51/00* (2006.01)
*C07D 251/24* (2006.01)
(Continued)

(52) U.S. Cl.
CPC ........ H01L 51/0067 (2013.01); C07D 251/24 (2013.01); C07D 401/08 (2013.01);
(Continued)

(58) Field of Classification Search
CPC .......... H01B 1/12; H01B 1/121; H01B 1/122; H01B 1/20; H01L 51/005; H01L 51/0062;
(Continued)

(56) References Cited

U.S. PATENT DOCUMENTS 8,815,418 B2 * 8/2014 Kim ........................ C09B 57/00
257/40
2018/0354934 A1 * 12/2018 He ........................ C07D 251/24

FOREIGN PATENT DOCUMENTS

WO 2017/065419 A1 4/2017
WO WO-2017065419 A1 * 4/2017 ......... H01L 51/0074
(Continued)

OTHER PUBLICATIONS

English language machine translation of Han et al. (WO 2017/171376 A1). (Year: 2017).*
(Continued)

*Primary Examiner* — Matthew R Diaz
(74) *Attorney, Agent, or Firm* — Eversheds Sutherland (US) LLP

(57) ABSTRACT

The present invention relates to compounds according to formula 1:

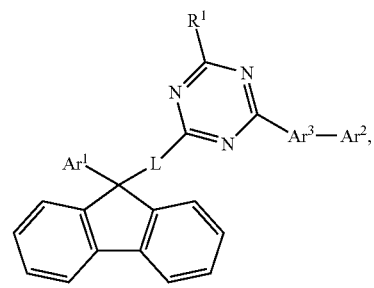

(1)

suitable for use as a layer material for electronic devices, and to an organic semiconductor layer comprising at least one compound according to formula 1, as well as to an organic
(Continued)

electronic device comprising at least one organic semiconductor layer thereof, and a method of manufacturing the same.

16 Claims, 2 Drawing Sheets

(51) Int. Cl.
    *C07D 401/10*    (2006.01)
    *H01B 1/12*      (2006.01)
    *C07D 407/04*    (2006.01)
    *C07D 407/14*    (2006.01)
    *C07D 401/08*    (2006.01)

(52) U.S. Cl.
    CPC ......... *C07D 401/10* (2013.01); *C07D 407/04* (2013.01); *C07D 407/14* (2013.01); *H01B 1/12* (2013.01)

(58) Field of Classification Search
    CPC . H01L 51/0067; C07D 251/24; C07D 251/26; C07D 401/08; C07D 401/10; C07D 407/04; C07D 407/14
    See application file for complete search history.

(56) References Cited

FOREIGN PATENT DOCUMENTS

| WO | WO-2017092619 A1 * | 6/2017 | ......... H01L 51/0072 |
| WO | 2017/171376 A1 | 10/2017 | |
| WO | WO-2017171376 A1 * | 10/2017 | ........... C07C 13/567 |

OTHER PUBLICATIONS

European Search Report for EP Application No. 17200890.6 dated Jan. 22, 2018 (6 pages).

* cited by examiner

COMPOUNDS COMPRISING TRIAZINE GROUP, FLUORENE-GROUP AND ARYL GROUP

CROSS REFERENCE TO RELATED APPLICATION

This application claims priority to European Patent Application No. 17200890.6, filed Nov. 9, 2017, which is incorporated herein by reference.

TECHNICAL FIELD

The present invention relates to compounds, in particular to compounds with a triazine group, fluorene group and aryl group, suitable for use as a layer material for electronic devices, and to an organic semiconductor layer comprising at least one compound thereof, as well as to an organic electronic device comprising at least one organic semiconductor layer thereof, and a method of manufacturing the same.

BACKGROUND ART

Organic electronic devices, such as organic light-emitting diodes OLEDs, which are self-emitting devices, have a wide viewing angle, excellent contrast, quick response, high brightness, excellent operating voltage characteristics, and color reproduction. A typical OLED comprises an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the organic semiconductor layer, and among them, may be affected by characteristics of an organic material of the organic semiconductor layer.

Particularly, development for an organic material being capable of increasing electron mobility and simultaneously increasing electrochemical stability is needed so that the organic electronic device, such as an organic light emitting diode, may be applied to a large-size flat panel display.

WO2017065419 relates to organic electroluminescent compounds, and a host material, an electron buffer material, an electron transport material and an organic electroluminescent device comprising the same. By using theganic electroluminescent compounds of the present disclosure, the organic electroluminescent device secures fast electron current properties by intermolecular stacking and interaction, and thus, it is possible to provide the organic electroluminescent device having low driving voltage and/or excellent luminous efficiency and/or efficient lifespan properties.

WO2017171376 relates to a compound of the chemical formula 1 and an organic electronic element comprising the compound.

There remains a need to improve performance of organic semiconductor layers, organic semiconductor materials, as well as organic electronic devices thereof, in particular to achieve increased lifetime and higher efficiency through improving the characteristics of the compounds comprised therein.

There is a need for alternative organic semiconductor materials and organic semiconductor layers as well as organic electronic devices having increased lifetime and/or improved efficiency at low operating voltage.

In particular there is a need for alternative compounds having increased lifetime as well as improved efficiency and at the same time keeping the operating voltage and thereby the power consumption low to deliver long battery life for example mobile electronic devices.

DISCLOSURE

An aspect of the present invention provides a compound of formula 1,

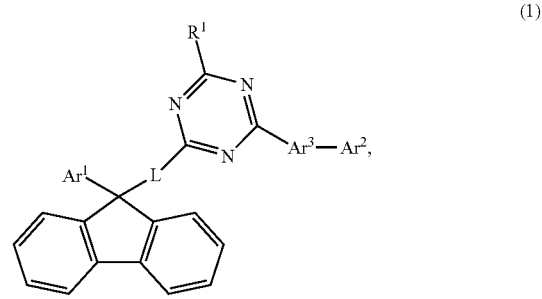

wherein
$R^1$ is selected from a $C_1$ to $C_{16}$ alkyl group, substituted or unsubstituted $C_6$ to $C_{24}$ aryl group, or a substituted or unsubstituted $C_2$ to $C_{24}$ heteroaryl group, wherein the substituent of the substituted $C_6$ to $C_{24}$ aryl group and of the substituted $C_2$ to $C_{24}$ heteroaryl group is selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, F, CN, $C_6$ to $C_{18}$ aryl or $C_3$ to $C_{25}$ heteroaryl;

L is selected from an unsubstituted or substituted $C_6$ to $C_{24}$ arylene group, wherein the substituents of the substituted $C_6$ to $C_{24}$ arylene group are selected from $C_1$ to $C_{16}$ alkyl or $C_6$ to $C_{12}$ aryl;

$Ar^1$ is selected from substituted or unsubstituted $C_6$ to $C_{24}$ aryl, or substituted or unsubstituted $C_2$ to $C_{24}$ heteroaryl, wherein the substituent of the substituted $C_6$ to $C_{24}$ aryl or substituted $C_2$ to $C_{24}$ heteroaryl is selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, F, $C_6$ to $C_{18}$ aryl or $C_3$ to $C_{25}$ heteroaryl;

$Ar^2$ is selected from the group comprising of —$C_6H_5CN$ or $C_2$ to $C_{24}$ heteroaryl containing N, O or S;

$Ar^3$ is selected from substituted or unsubstituted $C_6$ to $C_{24}$ arylene or substituted or unsubstituted $C_2$ to $C_{24}$ heteroarylene, wherein the substituent of the substituted $C_6$ to $C_{24}$ arylene or the substituent of the substituted $C_2$ to $C_{24}$ heteroarylene is selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, F, $C_6$ to $C_{18}$ aryl or $C_3$ to $C_{25}$ heteroaryl;

wherein
substituted $C_6$ to $C_{24}$ aryl or substituted $C_2$ to $C_{24}$ heteroaryl of $Ar^1$ is mono or di-substituted; and wherein
substituted $C_6$ to $C_{24}$ arylene or substituted $C_2$ to $C_{24}$ heteroarylene of $Ar^3$ is mono or di-substituted.

According to another embodiment, the compound according to formula 1 can be free of $C_1$ to $C_{16}$ alkoxy.

According to another embodiment, the compound according to formula 1 can be free of partially or perfluorinated $C_1$ to $C_{16}$ alkyl, partially or perfluorinated $C_1$ to $C_{16}$ alkoxy and/or F.

According to another embodiment, the compound according to formula 1 can be free of $C_1$ to $C_{16}$ alkoxy, partially or perfluorinated $C_1$ to $C_{16}$ alkyl, partially or perfluorinated $C_1$ to $C_{16}$ alkoxy and/or F.

According to another embodiment, the compound according to formula 1 can be defined:

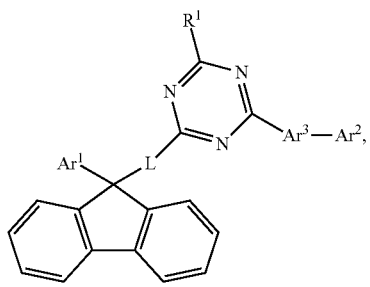

(1)

wherein
$R^1$ is selected from a $C_1$ to $C_{16}$ alkyl group, substituted or unsubstituted $C_6$ to $C_{24}$ aryl group, or a substituted or unsubstituted $C_2$ to $C_{24}$ heteroaryl group, wherein the substituent of the substituted $C_6$ to $C_{24}$ aryl group and of the substituted $C_2$ to $C_{24}$ heteroaryl group is selected from $C_1$ to $C_{16}$ alkyl, $C_6$ to $C_{18}$ aryl or $C_3$ to $C_{25}$ heteroaryl;

L is selected from an unsubstituted or substituted $C_6$ to $C_{24}$ arylene group, wherein the substituents of the substituted $C_6$ to $C_{24}$ arylene group are selected from $C_1$ to $C_{16}$ alkyl or $C_6$ to $C_{12}$ aryl;

$Ar^1$ is selected from substituted or unsubstituted $C_6$ to $C_{24}$ aryl, or substituted or unsubstituted $C_2$ to $C_{24}$ heteroaryl, wherein the substituent of the substituted $C_6$ to $C_{24}$ aryl or substituted $C_2$ to $C_{24}$ heteroaryl is selected from $C_1$ to $C_{16}$ alkyl, $C_6$ to $C_{18}$ aryl or $C_3$ to $C_{25}$ heteroaryl;

$Ar^2$ is selected from the group comprising of —$C_6H_5CN$ or $C_2$ to $C_{24}$ heteroaryl containing N, O or S;

$Ar^3$ is selected from substituted or unsubstituted $C_6$ to $C_{24}$ arylene or substituted or unsubstituted $C_2$ to $C_{24}$ heteroarylene, wherein the substituent of the substituted $C_6$ to $C_{24}$ arylene or the substituent of the substituted $C_2$ to $C_{24}$ heteroarylene is selected from $C_1$ to $C_{16}$ alkyl, $C_6$ to $C_{18}$ aryl or $C_3$ to $C_{25}$ heteroaryl;

wherein
substituted $C_6$ to $C_{24}$ aryl or substituted $C_2$ to $C_{24}$ heteroaryl of $Ar^1$ is mono or di-substituted; and
wherein
substituted $C_6$ to $C_{18}$ arylene or substituted $C_3$ to $C_{24}$ heteroarylene of $Ar^3$ is mono or di-substituted.

The $Ar^1$ group is connected via a single bond to a fluorene group of the compound of formula 1.

Mono or di-substituted $Ar^1$ means throughout the specification that for mono-substituted $Ar^1$ the $Ar^1$ group comprises one additional substituent and for di-substituted $Ar^1$ the $Ar^1$ group comprises two additional substituents, which can be independently selected.

The $Ar^2$ group is connected via a single bond to the $Ar^3$ group of the compound of formula 1.

The $Ar^2$ group can be selected from the group comprising of —$C_6H_5CN$ or $C_2$ to $C_{24}$ heteroaryl containing N, O or S, preferably $C_2$ to $C_{24}$ heteroaryl containing N or O and further preferred $C_2$ to $C_{24}$ heteroaryl containing O.

The $Ar^3$ group is connected via a single bond to the triazine group of the compound of formula 1.

Mono or di-substituted $Ar^3$ means throughout the specification that for mono-substituted $Ar^3$ the $Ar^3$ group comprises one additional substituent and for di-substituted $Ar^3$ the $Ar^3$ group comprises two additional substituents, which can be independently selected.

Hetero atoms if not otherwise stated can be individually selected from the group comprising N, O, S, B, Si, P, Se, preferably selected from the group comprising N, O and S, further preferred from the group comprising N and O, and in addition preferred the hetero atom is N.

According to one embodiment the compound represented by formula 1 can be free of a carbazolylene group.

According to one embodiment the compound of formula 1,

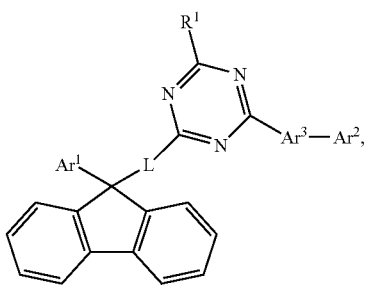

(1)

can be further defined, wherein
$R^1$ can be selected from a $C_1$ to $C_{12}$ alkyl group, substituted or unsubstituted $C_6$ to $C_{18}$ aryl group, or a substituted or unsubstituted $C_2$ to $C_{18}$ heteroaryl group, wherein
the substituent of the substituted $C_6$ to $C_{18}$ aryl group and of the substituted $C_2$ to $C_{18}$ heteroaryl group can be selected from $C_1$ to $C_{12}$ alkyl, $C_1$ to $C_{12}$ alkoxy, partially or perfluorinated $C_1$ to $C_{12}$ alkyl, partially or perfluorinated $C_1$ to $C_{12}$ alkoxy, F, CN, $C_6$ to $C_{18}$ aryl or $C_3$ to $C_{18}$ heteroaryl;

L can be selected from an unsubstituted or substituted $C_6$ to $C_{18}$ arylene group, wherein the substituents of the substituted $C_6$ to $C_{18}$ arylene group are selected from $C_1$ to $C_{12}$ alkyl or $C_6$ to $C_{12}$ aryl;

$Ar^1$ can be selected from substituted or unsubstituted $C_6$ to $C_{18}$ aryl or substituted or unsubstituted $C_3$ to $C_{18}$ heteroaryl, wherein
the substituents of the substituted $C_6$ to $C_{18}$ aryl and substituted or unsubstituted $C_3$ to $C_{24}$ heteroaryl are selected from $C_1$ to $C_{12}$ alkyl, $C_1$ to $C_{12}$ alkoxy, partially or perfluorinated $C_1$ to $C_{12}$ alkyl, partially or perfluorinated $C_1$ to $C_{12}$ alkoxy, F, $C_6$ to $C_{18}$ aryl, $C_3$ to $C_{18}$ heteroaryl or CN;

$Ar^2$ can be selected from the group comprising of —$C_6H_5CN$ or $C_2$ to $C_{18}$ heteroaryl containing N, O or S;

$Ar^3$ can be selected from substituted or unsubstituted $C_6$ to $C_{18}$ arylene or substituted or unsubstituted $C_2$ to $C_{18}$ heteroarylene, wherein the substituent of the substituted $C_6$ to $C_{18}$ arylene or the substituent of the substituted $C_2$ to $C_{18}$ heteroarylene is selected from $C_1$ to $C_{12}$ alkyl, $C_6$ to $C_{18}$ aryl or $C_3$ to $C_{18}$ heteroaryl;

wherein substituted $C_6$ to $C_{18}$ aryl or substituted $C_3$ to $C_{18}$ heteroaryl of $Ar^1$ is mono or di-substituted; and wherein substituted $C_6$ to $C_{18}$ arylene or substituted $C_2$ to $C_{18}$ heteroarylene of $Ar^3$ is mono or di-substituted.

According to another embodiment the compound of formula 1,

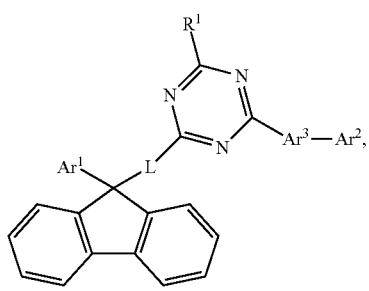

(1)

can be further defined, wherein $R^1$ can be selected from a substituted or unsubstituted $C_6$ to $C_{18}$ aryl group, or a substituted or unsubstituted $C_2$ to $C_{18}$ heteroaryl group, wherein the substituent of the substituted $C_6$ to $C_{18}$ aryl group and of the substituted $C_2$ to $C_{18}$ heteroaryl group can be selected from $C_1$ to $C_{12}$ alkyl, $C_6$ to $C_{18}$ aryl or $C_3$ to $C_{18}$ heteroaryl;

L can be selected from an unsubstituted or substituted $C_6$ to $C_{12}$ arylene group, wherein the substituents of the substituted $C_6$ to $C_{12}$ arylene group are selected from $C_1$ to $C_{12}$ alkyl or $C_6$ to $C_{12}$ aryl;

$Ar^1$ can be selected from substituted or unsubstituted $C_6$ to $C_{18}$ aryl, wherein the substituents of the substituted $C_6$ to $C_{18}$ aryl are selected from $C_1$ to $C_{12}$ alkyl, $C_6$ to $C_{18}$ aryl, $C_3$ to $C_{18}$ heteroaryl or CN;

$Ar^2$ can be selected from the group comprising of —$C_6H_5CN$ or $C_2$ to $C_{17}$ heteroaryl containing N, O or S;

$Ar^3$ can be selected from substituted or unsubstituted $C_6$ to $C_{18}$ arylene, wherein the substituent of the substituted $C_6$ to $C_{18}$ arylene is selected from $C_1$ to $C_{12}$ alkyl, $C_6$ to $C_{18}$ aryl or $C_3$ to $C_{18}$ heteroaryl;

wherein substituted $C_6$ to $C_{18}$ aryl of $Ar^1$ is mono or di-substituted; and wherein substituted $C_6$ to $C_{18}$ arylene of $Ar^3$ is mono or di-substituted.

According to another embodiment the compound of formula 1,

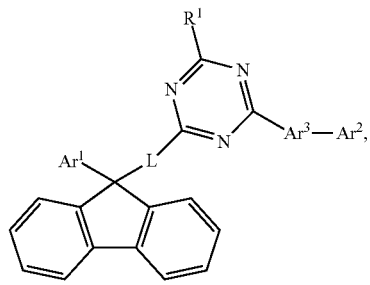

(1)

can be further defined, wherein $R^1$ can be selected from a group comprising phenyl, biphenyl, fluorene, dibebenzothiophenyl or dibenzofuranyl;

L can be selected from an unsubstituted $C_6$ to $C_{12}$ arylene group;

$Ar^1$ can be selected from an unsubstituted $C_6$ to $C_{18}$ aryl group;

$Ar^2$ can be selected from the group comprising of —$C_6H_5CN$ or $C_2$ to $C_{17}$ heteroaryl containing N, O or S;

$Ar^3$ can be selected from unsubstituted $C_6$ to $C_{18}$ arylene.

According to another embodiment the compound of formula 1,

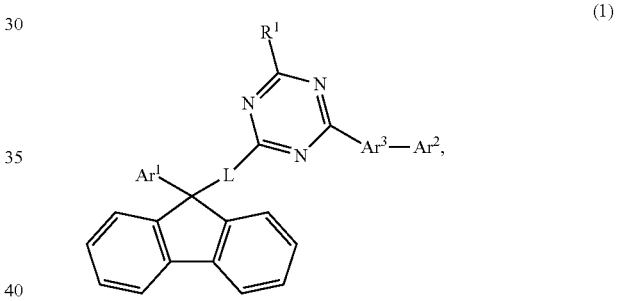

(1)

can be further defined, wherein $R^1$ can be selected from a group comprising phenyl, biphenyl, dibebenzothiophenyl or dibenzofuranyl;

L can be selected from phenylene or biphenylene;

$Ar^1$ can be selected from phenyl or biphenyl;

$Ar^2$ can be selected from the group comprising of —$C_6H_5CN$ or $C_2$ to $C_{11}$ heteroaryl containing N, O or S;

$Ar^3$ can be selected from phenylene or biphenylene.

According to another embodiment the compound of formula 1,

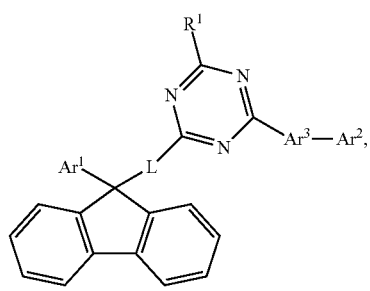

(1)

can be further defined, wherein
$R^1$ can be selected from a group comprising phenyl;
L can be selected from phenylene;
$Ar^1$ can be selected from phenyl;
$Ar^2$ can be selected from the group comprising of —$C_6H_5CN$;
$Ar^3$ can be selected from phenylene.

According to another embodiment the compound of formula 1,

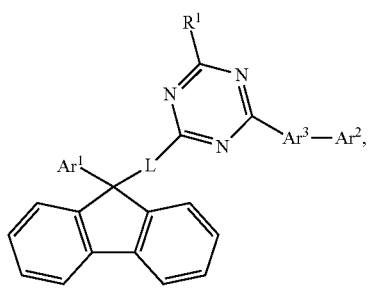

(1)

can be further defined, wherein
$R^1$ can be selected from dibenzofuranyl;
L can be selected from phenylene;
$Ar^1$ can be selected from phenyl;
$Ar^2$ can be selected from $C_2$ to $C_{11}$ heteroaryl containing at least one N;
$Ar^3$ can be selected from phenylene.

According to one embodiment $R^1$ can be selected from a substituted $C_6$ to $C_{24}$ aryl group, or a substituted $C_2$ to $C_{24}$ heteroaryl group, wherein the substituent of the substituted $C_6$ to $C_{24}$ aryl group and of the substituted $C_2$ to $C_{24}$ heteroaryl group is selected from $C_1$ to $C_{16}$ alkyl, $C_6$ to $C_{18}$ aryl or $C_3$ to $C_{25}$ heteroaryl.

According to one embodiment $R^1$ can be selected from a $C_1$ to $C_{16}$ alkyl group, unsubstituted $C_6$ to $C_{24}$ aryl group, or unsubstituted $C_2$ to $C_{24}$ heteroaryl group.

According to one embodiment $R^1$ can be selected from a substituted $C_6$ to $C_{18}$ aryl group, or a substituted $C_2$ to $C_{17}$ heteroaryl group, wherein the substituent of the substituted $C_6$ to $C_{18}$ aryl group and of the substituted $C_2$ to $C_{17}$ heteroaryl group is selected from $C_1$ to $C_{16}$ alkyl, $C_6$ to $C_{18}$ aryl or $C_3$ to $C_{17}$ heteroaryl.

According to one embodiment $R^1$ can be selected from a $C_1$ to $C_{12}$ alkyl group, unsubstituted $C_6$ to $C_{18}$ aryl group, or unsubstituted $C_2$ to $C_{17}$ heteroaryl group.

According to one embodiment $R^1$ can be selected from a substituted $C_6$ to $C_{12}$ aryl group, or a substituted $C_2$ to $C_{11}$ heteroaryl group, wherein the substituent of the substituted $C_6$ to $C_{12}$ aryl group and of the substituted $C_2$ to $C_{11}$ heteroaryl group is selected from $C_1$ to $C_{12}$ alkyl, $C_6$ to $C_{12}$ aryl or $C_3$ to $C_{11}$ heteroaryl.

According to one embodiment $R^1$ can be selected from a $C_1$ to $C_6$ alkyl group, unsubstituted $C_6$ to $C_{12}$ aryl group, or unsubstituted $C_2$ to $C_{11}$ heteroaryl group.

According to one embodiment $R^1$ can be selected from an unsubstituted $C_6$ to $C_{12}$ aryl group, or unsubstituted $C_2$ to $C_{11}$ heteroaryl group, preferably dibenzofuranyl.

According to one embodiment $R^1$ can be selected from an unsubstituted $C_6$ to $C_{12}$ aryl group, preferably phenyl group.

According to one embodiment, L can be selected from an unsubstituted or substituted $C_6$ to $C_{18}$ arylene group, wherein the substituents of the substituted $C_6$ to $C_{18}$ arylene group are selected from $C_1$ to $C_{16}$ alkyl or $C_6$ to $C_{12}$ aryl.

According to one embodiment, L can be selected from an unsubstituted $C_6$ to $C_{18}$ arylene group.

According to one embodiment, L can be selected from a substituted $C_6$ to $C_{18}$ arylene group, wherein the substituents of the substituted $C_6$ to $C_{18}$ arylene group are selected from $C_1$ to $C_{16}$ alkyl or $C_6$ to $C_{12}$ aryl.

According to one embodiment, L can be selected from an unsubstituted $C_6$ to $C_{12}$ arylene group.

According to one embodiment, L can be selected from a substituted $C_6$ to $C_{12}$ arylene group, wherein the substituents of the substituted $C_6$ to $C_{12}$ arylene group are selected from $C_6$ to $C_{12}$ aryl.

According to one embodiment, L can be selected from phenylene or biphenylene, preferably phenylene.

According to one embodiment, L can be selected from a substituted phenylene or biphenylene, preferably phenylene, wherein the substituents of the substituted phenylene or biphenylene are selected from $C_1$ to $C_3$ alkyl or $C_6$ to $C_{12}$ aryl.

According to one embodiment, $Ar^1$ can be selected from a substituted $C_6$ to $C_{24}$ aryl group, or a substituted $C_2$ to $C_{24}$ heteroaryl group, wherein the substituent of the substituted $C_6$ to $C_{24}$ aryl group and of the substituted $C_2$ to $C_{24}$ heteroaryl group is selected from $C_1$ to $C_{16}$ alkyl, $C_6$ to $C_{18}$ aryl or $C_3$ to $C_{25}$ heteroaryl.

According to one embodiment, $Ar^1$ can be selected from an unsubstituted $C_6$ to $C_{24}$ aryl group, or unsubstituted $C_2$ to $C_{24}$ heteroaryl group.

According to one embodiment, $Ar^1$ can be selected from a substituted $C_6$ to $C_{18}$ aryl group, or a substituted $C_2$ to $C_{17}$ heteroaryl group, wherein the substituent of the substituted $C_6$ to $C_{18}$ aryl group and of the substituted $C_2$ to $C_{17}$ heteroaryl group is selected from $C_1$ to $C_{16}$ alkyl, $C_6$ to $C_{18}$ aryl or $C_3$ to $C_{17}$ heteroaryl.

According to one embodiment, $Ar^1$ can be selected from an unsubstituted $C_6$ to $C_{18}$ aryl group, or unsubstituted $C_2$ to $C_{17}$ heteroaryl group.

According to one embodiment, $Ar^1$ can be selected from a substituted $C_6$ to $C_{12}$ aryl group, or a substituted $C_2$ to $C_{11}$ heteroaryl group, wherein the substituent of the substituted $C_6$ to $C_{12}$ aryl group and of the substituted $C_2$ to $C_{11}$ heteroaryl group is selected from $C_1$ to $C_{12}$ alkyl, $C_6$ to $C_{12}$ aryl or $C_3$ to $C_{11}$ heteroaryl.

According to one embodiment, $Ar^1$ can be selected from an unsubstituted $C_6$ to $C_{12}$ aryl group, or unsubstituted $C_2$ to $C_{11}$ heteroaryl group.

According to one embodiment, $Ar^1$ can be selected from an unsubstituted $C_6$ to $C_{12}$ aryl group, or unsubstituted $C_2$ to $C_{11}$ heteroaryl group, preferably a phenyl or biphenyl group.

According to one embodiment, $Ar^1$ can be selected from a phenyl group.

According to one embodiment, $Ar^2$ can be selected from —$C_6H_5CN$ or $C_2$ to $C_{23}$ heteroaryl containing N, O or S.

When $Ar^2$ is selected from this group, particularly good performance may be achieved.

Without being bound by theory, the group comprising —$C_6H_5CN$ or $C_2$ to $C_{23}$ heteroaryl containing N, O or S may impart a dipole moment above 0.6 Debye on the compound of formula 1.

It is believed that a high dipole moment may improve interaction between the compound of formula 1 and the dopant material, if present. In particular, if the dopant material is selected from a metal halide and/or metal complex, improved performance may be obtained.

According to one embodiment, $Ar^2$ can be selected from —$C_6H_5CN$ or $C_2$ to $C_{17}$ heteroaryl containing N, O or S, preferably N.

According to one embodiment, $Ar^2$ can be selected from —$C_6H_5CN$ or $C_2$ to $C_{11}$ heteroaryl containing N, O or S, preferably N.

According to one embodiment, $Ar^2$ can be selected from —$C_6H_5CN$.

According to one embodiment, $Ar^2$ can be selected from $C_2$ to $C_{11}$ heteroaryl containing N.

According to one embodiment of formula 1, wherein $Ar^2$ comprising a triazinyl, carbazolyl and/or indolo-carbazolyl group are excluded.

According to one embodiment of formula 1, wherein $Ar^2$ comprising a triazinyl, group are excluded.

According to one embodiment of formula 1, wherein $Ar^2$ comprising a carbazolyl group are excluded.

According to one embodiment of formula 1, wherein $Ar^2$ comprising a indolo-carbazolyl group are excluded.

According to one embodiment of formula 1, wherein $Ar^2$ may be selected from —$C_6H_5CN$, pyridinyl, pyrimidinyl, quinolinyl, benzimidazolyl, benzothiazolyl, benzooxazolyl, dibenzofuranyl or dibenzothiophenyl.
Particularly good performance may be obtained when $Ar^2$ is selected from these groups.

According to one embodiment, $Ar^3$ can be selected from a substituted $C_6$ to $C_{24}$ arylene group, or a substituted $C_2$ to $C_{24}$ heteroarylene group, wherein the substituent of the substituted $C_6$ to $C_{24}$ arylene group and of the substituted $C_2$ to $C_{24}$ heteroarylene group is selected from $C_1$ to $C_{16}$ alkyl, $C_6$ to $C_{18}$ arylene or $C_3$ to $C_{25}$ heteroarylene.

According to one embodiment, $Ar^3$ can be selected from an unsubstituted $C_6$ to $C_{24}$ arylene group, or unsubstituted $C_2$ to $C_{24}$ heteroarylene group.

According to one embodiment, $Ar^3$ can be selected from a substituted $C_6$ to $C_{18}$ arylene group, or a substituted $C_2$ to $C_{17}$ heteroarylene group, wherein the substituent of the substituted $C_6$ to $C_{18}$ arylene group and of the substituted $C_2$ to $C_{17}$ heteroarylene group is selected from $C_1$ to $C_{16}$ alkyl, $C_6$ to $C_{18}$ arylene or $C_3$ to $C_{17}$ heteroarylene.

According to one embodiment, $Ar^3$ can be selected from an unsubstituted $C_6$ to $C_{18}$ arylene group, or unsubstituted $C_2$ to $C_{17}$ heteroarylene group.

According to one embodiment, $Ar^3$ can be selected from a substituted $C_6$ to $C_{12}$ arylene group, or a substituted $C_2$ to $C_{11}$ heteroarylene group, wherein the substituent of the substituted $C_6$ to $C_{12}$ arylene group and of the substituted $C_2$ to $C_{11}$ heteroarylene group is selected from $C_1$ to $C_{12}$ alkyl, $C_6$ to $C_{12}$ arylene or $C_3$ to $C_{11}$ heteroarylene.

According to one embodiment, $Ar^3$ can be selected from an unsubstituted $C_6$ to $C_{12}$ arylene group, or unsubstituted $C_2$ to $C_{11}$ heteroarylene group.

According to one embodiment, $Ar^3$ can be selected from an unsubstituted $C_6$ to $C_{12}$ arylene group, or unsubstituted $C_2$ to $C_{11}$ heteroarylene group, preferably a phenylene or biphenylene group.

According to one embodiment, $Ar^3$ can be selected from a phenylene group.

According to one embodiment, substituted $C_6$ to $C_{24}$ aryl or substituted $C_2$ to $C_{24}$ heteroaryl of $Ar^1$ can be mono substituted.

According to one embodiment, substituted $C_6$ to $C_{18}$ arylene or substituted $C_3$ to $C_{24}$ heteroarylene of $Ar^3$ can be mono substituted.

According to one embodiment, substituted $C_6$ to $C_{24}$ aryl or substituted $C_2$ to $C_{24}$ heteroaryl of $Ar^1$ can be di-substituted.

According to one embodiment, substituted $C_6$ to $C_{18}$ arylene or substituted $C_3$ to $C_{24}$ heteroarylene of $Ar^3$ can be di-substituted.

According to another embodiment, formula 1 may comprises at least about 5 to about 16 $C_6$ aryl rings.

According to another embodiment, formula 1 may comprises at least about 5 to about 16 $C_6$ aryl rings and at least about 1 to about 5 six-member hetero aryl rings, wherein the hetero atoms can be individually selected from N, O, S, preferably N.

According to an aspect the compound of formula 1 can be used as a matrix material for a dopant material.

According to an aspect, the layer material can be an organic semiconductor layer, which is used for an organic electronic device. For example, the organic electronic device can be an OLED or there like.

The compounds represented by formula 1 and an organic semiconductor layer consisting or comprising of a compound of formula 1 may be non-emissive.

In the context of the present specification the term "essentially non-emissive" or "non-emitting" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconductor layer comprising the compound of formula 1 is essentially non-emissive or non-emitting.

The term "free of", "does not contain", "does not comprise" does not exclude impurities which may be present in the compounds prior to deposition. Impurities have no technical effect with respect to the object achieved by the present invention.

The operating voltage, also named U, is measured in Volt (V) at 10 milliAmpere per square centimeter (mA/cm2).

The candela per Ampere efficiency, also named cd/A efficiency, is measured in candela per ampere at 10 milli-Ampere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are calculated in electron volt (eV).

The reduction potential is measured by cyclic voltammetry in Volt (V).

The term "OLED", "organic light emitting diode", "organic light emitting device", "organic optoelectronic device" and "organic light-emitting diode" are simultaneously used and have the same meaning.

The term "transition metal" means and comprises any element in the d-block of the periodic table, which comprises groups 3 to 12 elements on the periodic table.

The term "group III to VI metal" means and comprises any metal in groups III to VI of the periodic table.

As used herein, "weight percent", "wt.-%", "percent by weight", "% by weight", and variations thereof refer to a composition, component, substance or agent as the weight of that composition, component, substance or agent of the respective electron transport layer divided by the total weight of the composition thereof and multiplied by 100. It is understood that the total weight percent amount of all components, substances or agents of the respective electron transport layer are selected such that it does not exceed 100 wt.-%.

As used herein, "volume percent", "vol.-%", "percent by volume", "% by volume", and variations thereof refer to an elemental metal, a composition, component, substance or agent as the volume of that elemental metal, component, substance or agent of the respective electron transport layer divided by the total volume of the respective electron transport layer thereof and multiplied by 100. It is understood that the total volume percent amount of all elemental metal, components, substances or agents of the respective cathode electrode layer are selected such that it does not exceed 100 vol.-%.

All numeric values are herein assumed to be modified by the term "about", whether or not explicitly indicated. As used herein, the term "about" refers to variation in the numerical quantity that can occur.

Whether or not modified by the term "about", the claims include equivalents to the quantities.

It should be noted that, as used in this specification and the appended claims, the singular forms "a", "an", and "the" include plural referents unless the content clearly dictates otherwise.

It should be noted that, as used in this specification and the appended claims, "*" if not otherwise defined indicates the chemical bonding position.

The anode electrode and cathode electrode may be described as anode electrode/cathode electrode or anode electrode/cathode electrode or anode electrode layer/cathode electrode layer.

According to another aspect, an organic optoelectronic device comprises an anode layer and a cathode layer facing each other and at least one organic semiconductor layer between the anode layer and the cathode layer, wherein the organic semiconductor layer comprises or consists of the compound of formula 1.

According to yet another aspect, a display device comprising the organic electronic device, which can be an organic optoelectronic device, is provided.

In the present specification, when a definition is not otherwise provided, an "alkyl group" may refer to an aliphatic hydrocarbon group. The alkyl group may refer to "a saturated alkyl group" without any double bond or triple bond. The alkyl group may be a linear, cyclic or branched alkyl group.

The alkyl group may be a $C_1$ to $C_{16}$ alkyl group, or preferably a $C_1$ to $C_{12}$ alkyl group. More specifically, the alkyl group may be a $C_1$ to $C_{14}$ alkyl group, or preferably a $C_1$ to $C_{10}$ alkyl group or a $C_1$ to $C_6$ alkyl group. For example, a $C_1$ to $C_4$ alkyl group comprises 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a tert-butyl group, a pentyl group, a hexyl group, a cyclopropyl group, a cyclobutyl group, a cyclopentyl group, a cyclohexyl group, and the like.

In the present specification, $R^2$ can be independently selected from H, $C_1$ to $C_{16}$ branched or linear alkyl, $C_6$ to $C_{18}$ aryl and $C_3$ to $C_{25}$ heteroaryl, preferably $R^2$ is $C_1$ to $C_6$ alkyl or $C_6$ to $C_{12}$ aryl.

In the present specification, when a definition is not otherwise provided, $R^2$ can be independently selected from H, $C_1$ to $C_{16}$ alkyl, $C_6$ to $C_{18}$ aryl.

In the present specification "arylene group" may refer to a group comprising at least one hydrocarbon aromatic moiety, and all the elements of the hydrocarbon aromatic moiety may have p-orbitals which form conjugation, for example a phenyl group, a naphthyl group, an anthracenyl group, a phenanthrenyl group, a pyrenyl group, a fluorenyl group and the like.

The arylene/aryl group may include a monocyclic, polycyclic or fused ring polycyclic (i.e., rings sharing adjacent pairs of carbon atoms) functional group.

The term "heteroarylene"/"heteroaryl" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S.

A heteroarylene/heteroaryl ring may comprise at least 1 to 3 heteroatoms. Preferably a heteroarylene/heteroaryl ring may comprise at least 1 to 3 heteroatoms individually selected from N, S and/or O.

Further preferred in addition to the triazine group of formula 1 at least one additional heteroaryl/ene ring may comprise at least 1 to 3 N-atoms, or at least 1 to 2-N atoms or at least one N-atom.

According to one embodiment in addition to the triazine group of formula 1, the compound of formula 1 may comprises one or two N-Atoms, preferably one N atom.

According to one embodiment in addition to the triazine group of formula 1, the compound of formula 1 may comprises one or two N-Atoms, preferably one N atom; and at least one or two O atoms, preferably one O atom.

The term "heteroarylene""/"heteroaryl" as used herewith shall encompass dibenzofurane, dibenzothiopene, pyridine, quinazoline, quinazoline, pyrimidine, triazine, benzimidazole, benzothiazole, benzoxazole, benzo[4,5]thieno[3,2-d]pyrimidine, xanthene, phenoxazine, benzoacridine, dibenzoacridine and the like.

In the present specification, the single bond refers to a direct bond.

According to another preferred embodiment, the compound according to formula 1 may comprise:
    at least 7 to 25 aromatic rings, preferably at least 8 to 22 aromatic rings, further preferred at least 9 to 20 aromatic rings, in addition preferred at least 10 to 15 aromatic rings and more preferred at least 10 to 14 aromatic rings; wherein
    at least 2 to 5, preferably 3 to 4 or 2 to 3, are heteroaromatic rings.

According to one embodiment, the compound according to formula 1:
    comprises at least about 8 to about 20 aromatic rings, preferably at least about 9 to about 18 aromatic rings, further preferred at least about 10 to about 16 aromatic rings, in addition preferred at least about 11 to about 15 aromatic rings and more preferred at least about 10 to about 14 aromatic rings; and/or
    the compound of formula 1 comprises at least about 2 to about 6, preferably about 3 to about 5 or about 2 to about 4, hetero aromatic rings, wherein the hetero atoms can be selected from N, O, S; and/or
    comprises at least one fluorene ring and at least one hetero-fluorene ring, wherein the hetero atoms can be selected from N, O, S; and/or
    comprises at least one triazine ring, and preferably at least two triazine rings.

According to one preferred embodiment, the compound according to formula 1 may comprises at least about 8 to about 20 aromatic rings, preferably at least about 9 to 18 aromatic rings, further preferred at least 10 to about 16 aromatic rings, in addition preferred at least 8 to 15 aromatic rings and more preferred at least about 10 to about 14 aromatic rings, wherein at least one of the aromatic rings is an unsubstituted five member ring and at least one of the aromatic rings is a five member hetero-ring.

According to one preferred embodiment, the compound according to formula 1 may comprises at least about 8 to about 20 aromatic rings, preferably at least about 9 to 18 aromatic rings, further preferred at least 10 to about 16 aromatic rings, in addition preferred at least 8 to 15 aromatic rings and more preferred at least about 10 to about 14 aromatic rings, wherein at least one of the aromatic rings is an unsubstituted five member ring and at least one of the aromatic rings is a five member hetero-ring.

According to a further preferred embodiment, the compound of formula 1 comprises at least 2 to 7, preferably 2 to 5, or 2 to 3 hetero aromatic rings.

According to a further preferred embodiment, the compound of formula 1 comprises at least 2 to 7, preferably 2 to 5, or 2 to 3 hetero aromatic rings, wherein at least one of the aromatic rings is a five member hetero aromatic ring.

According to a further preferred embodiment, the compound of formula 1 comprises at least 3 to 7, preferably 3 to 6, or 3 to 5 hetero aromatic rings, wherein at least two of the hetero aromatic rings are five member hetero-aromatic-ring.

According to one embodiment, the compound according to formula 1 may comprise at least 6 to 12 non-hetero aromatic rings and 2 to 3 hetero aromatic rings.

According to one preferred embodiment, the compound according to formula 1 may comprise at least 7 to 12 non-hetero aromatic rings and 2 to 5 hetero aromatic rings.

According to one preferred embodiment the compound according to formula 1 may comprise at least 7 to 11 non-hetero aromatic rings and 2 to 3 hetero aromatic rings.

The term "$C_6$-arylene/aryl ring" means single $C_6$-arylene/aryl rings and $C_6$-arylene/aryl rings which form condensed ring systems. For example, a naphthalene group would be counted as two $C_6$-arylene/aryl rings.

According to another embodiment, the compound of formula 1 may have a glass transition temperature Tg of about ≥100° C. and about ≤380° C., preferably about ≥105° C. and about ≤350° C., further preferred about ≥110° C. and about ≤320° C., in addition preferred about ≥115° C. and about ≤200° C. and also preferred about ≥125° C. and about ≤180° C.

According to another embodiment the compound of formula 1 may have a glass transition temperature Tg of about ≥120° C. and about ≤150° C.

The glass transition temperature is measured under nitrogen and using a heating rate of 10 K per min in a Mettler Toledo DSC 822e differential scanning calorimeter as described in DIN EN ISO 11357, published in March 2010.

Room temperature, also named ambient temperature, is 23° C.

Surprisingly, it was found that the compounds of formula 1 and the inventive organic electronic devices solve the problem underlying the present invention by being superior over the organic electroluminescent devices and compounds known in the art, in particular with respect to cd/A efficiency, also referred to as current efficiency and to lifetime. At the same time the operating voltage is kept at a similar or even improved level which is important for reducing power consumption and increasing battery life, for example of a mobile display device. High cd/A efficiency is important for high efficiency and thereby increased battery life of a mobile device, for example a mobile display device. Long lifetime is important for the longevity of a device.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned property of cd/A efficiency and lifetime. These compounds are discussed herein to be particularly preferred.

Further an organic optoelectronic device having high efficiency and/or long lifetime may be realized.

According to one embodiment of the compound according to formula 1, wherein $Ar^2$ may comprises at least one heteroaryl/ene that comprises at least one N or at least one CN substituent; and further preferred $Ar^1$ and $Ar^3$ may be free of a heteroatom and $Ar^2$ may comprises at least one heteroaryl/ene that comprises at least one N, and/or at least one CN substituent.

The abbreviation "heteroaryl/ene" stands for heteroaryl or heteroarylene.

According to one embodiment of the compound according to formula 1, wherein $Ar^2$ may have electron acceptor properties.

"Electron acceptor properties" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, page 477.

Especially, if compound of formula 1 is used as an electron transport or electron injection material, particularly good performance may be achieved, when $Ar^2$ has electron acceptor properties.

According to one embodiment of the compound according to formula 1, wherein the dipole moment of compound of formula 1 is >0.6 Debye and ≤10 Debye; and wherein the calculated HOMO is more negative than −5.4 eV.

According to one embodiment of the compound according to formula 1, wherein the dipole moment of compound of formula 1 is >0.6 Debye and ≤10 Debye; and wherein the calculated HOMO is more negative than −5.4 eV and less negative than −8 eV.

Preferably, the dipole moment of compound of formula 1 is >1 Debye and ≤10 Debye, even more preferred >2 Debye and ≤10 Debye, also preferred >3 Debye and ≤10 Debye. Preferably, the calculated HOMO is more negative than −5.6 eV, even more preferred more negative than −5.8 eV.

The dipole moment $|\vec{\mu}|$ of a molecule containing N atoms is given by:

$$\vec{\mu} = \sum_i^N q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The geometries of the molecular structures are optimized by applying the hybrid functional B3LYP with the 6-31G* basis set as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the bond lengths of the molecules.

When the dipole moment is selected in this range, particularly good performance may be obtained, in particular when used together with a dopant material.

The HOMO is calculated with the program package TURBOMOLE V6.5. The optimized geometries and the HOMO energy levels of the molecular structures are determined by applying the hybrid functional B3LYP with a 6-31G* basis set. If more than one conformation is viable, the conformation with the lowest total energy is selected.

Compounds with a HOMO in this range typically have electron acceptor properties. Particularly good performance may be obtained when the HOMO is selected in this range, especially when the compound of formula 1 is used as matrix compound in an electron transport and/or electron injection layer.

According to one embodiment of the compound according to formula 1, wherein $R^1$ is selected from a $C_1$ to $C_{12}$ alkyl group or unsubstituted $C_6$ to $C_{12}$ aryl group, preferably an unsubstituted $C_6$ to $C_{12}$ aryl group, further preferred an unsubstituted $C_6$ arylene group;

L is selected from an unsubstituted $C_6$ to $C_{12}$ arylene group, preferably an unsubstituted $C_6$ arylene group;

$Ar^1$ is selected from an unsubstituted $C_6$ to $C_{18}$ aryl, preferably an unsubstituted $C_6$ to $C_{12}$ aryl group, further preferred an unsubstituted phenyl group;

$Ar^3$ is selected from an unsubstituted $C_6$ to $C_{18}$ arylene, preferably an unsubstituted $C_6$ to $C_{12}$ arylene group, further preferred an unsubstituted phenylene group; and $Ar^2$ is selected from the group comprising of —$C_6H_5CN$ or $C_2$ to $C_{24}$ N-containing heteroaryl, preferably —$C_6H_5CN$.

According to one embodiment of the compound according to formula 1, wherein $R^1$ is independently selected from B1 to B16, B17 to B20 and B21 to B25, preferably selected from phenyl, biphenyl, terphenyl, naphthyl, phenanthrenyl, pyrenyl;

$R^2$ is independently selected from H, $C_1$ to $C_{16}$ alkyl, $C_6$ to $C_{18}$ aryl and $C_3$ to $C_{25}$ heteroaryl, preferably $R^2$ is $C_1$ to $C_6$ alkyl or $C_6$ to $C_{12}$ aryl;

wherein B1 to B11 are unsubstituted aryl groups and B12 to B16 are substituted aryl groups:

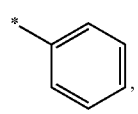

B1

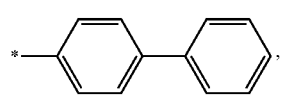

B2

-continued

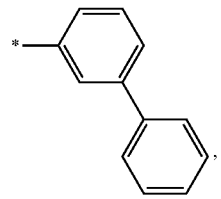

B3

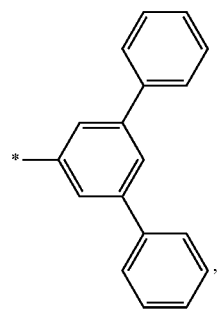

B4

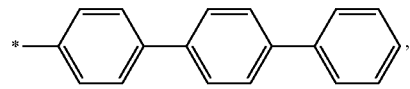

B5

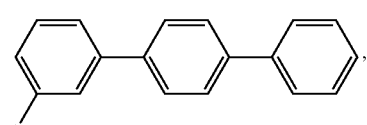

B6

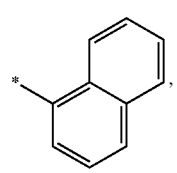

B7

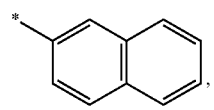

B8

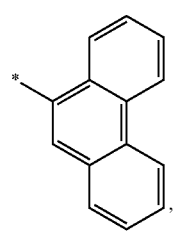

B9

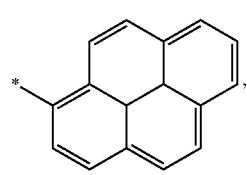

B10

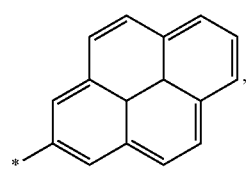

B11

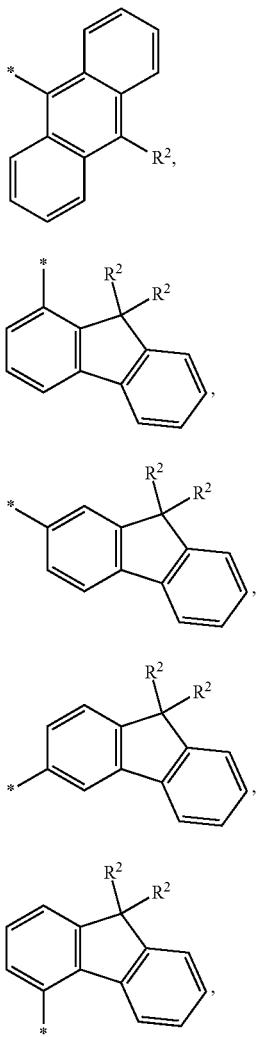

wherein B17 to B20 are unsubstituted dibenzofuranyl groups:

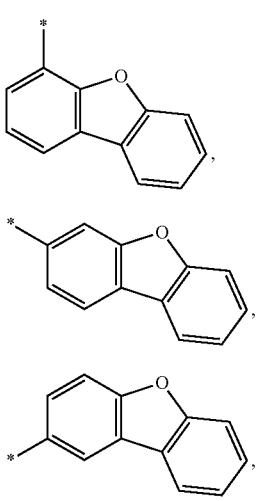

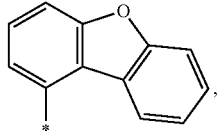

wherein B21 to B25 are unsubstituted dibebenzothiophenyl groups:

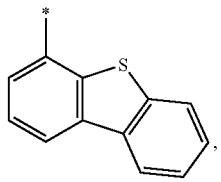

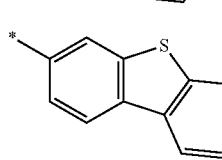

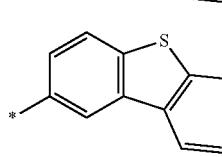

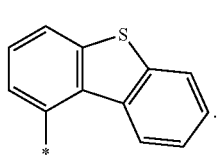

According to one embodiment of the compound according to formula 1, wherein $R^1$ is independently selected from B1 to B6.

According to one embodiment of the compound according to formula 1, wherein $R^1$ is independently selected from B7 to B12.

According to one embodiment of the compound according to formula 1, wherein $R^1$ is independently selected from B13 to B16.

According to one embodiment of the compound according to formula 1, wherein $R^1$ is independently selected from B17 to B20.

According to one embodiment of the compound according to formula 1, wherein $R^1$ is independently selected from B21 to B25.

According to one embodiment of the compound according to formula 1, wherein $Ar^1$ is independently selected from B1 to B25, and preferably selected from phenyl, biphenyl, terphenyl, naphthyl, and further more selected from phenyl.

According to one embodiment of the compound according to formula 1, wherein $Ar^1$ is independently selected from B1 to B6.

According to one embodiment of the compound according to formula 1, wherein $Ar^1$ is independently selected from B7 to B12.

According to one embodiment of the compound according to formula 1, wherein $Ar^1$ is independently selected from B13 to B16.

According to one embodiment of the compound according to formula 1, wherein Ar¹ is independently selected from B17 to B20.

According to one embodiment of the compound according to formula 1, wherein Ar¹ is independently selected from B21 to B25.

According to one embodiment of the compound according to formula 1, Ar³ is selected from C1 to C13:

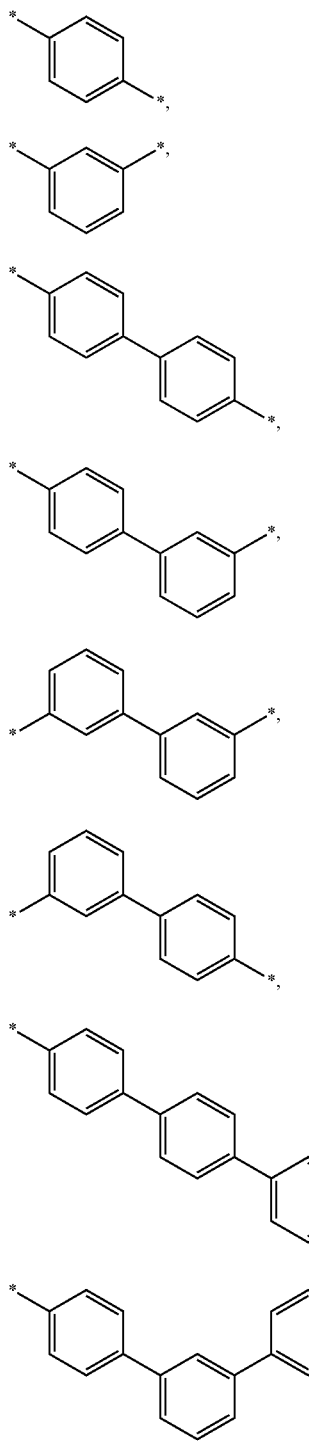

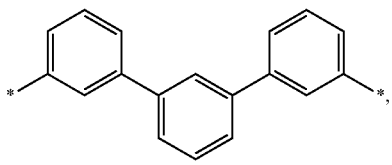

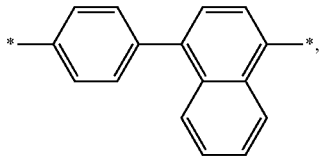

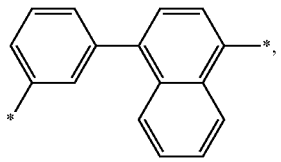

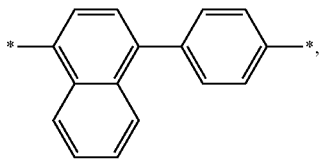

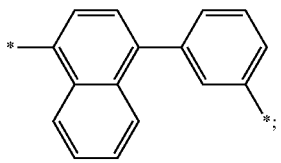

and
preferably Ar³ is selected from C1 to C9, and more preferred Ar³ is selected from C2, C4 to C6 and C8 to C9.

According to one embodiment of the compound according to formula 1, L can be selected from C1 to C13:

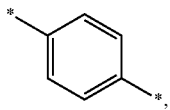

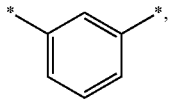

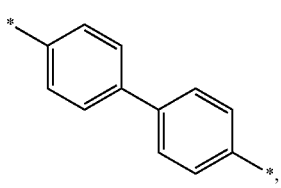

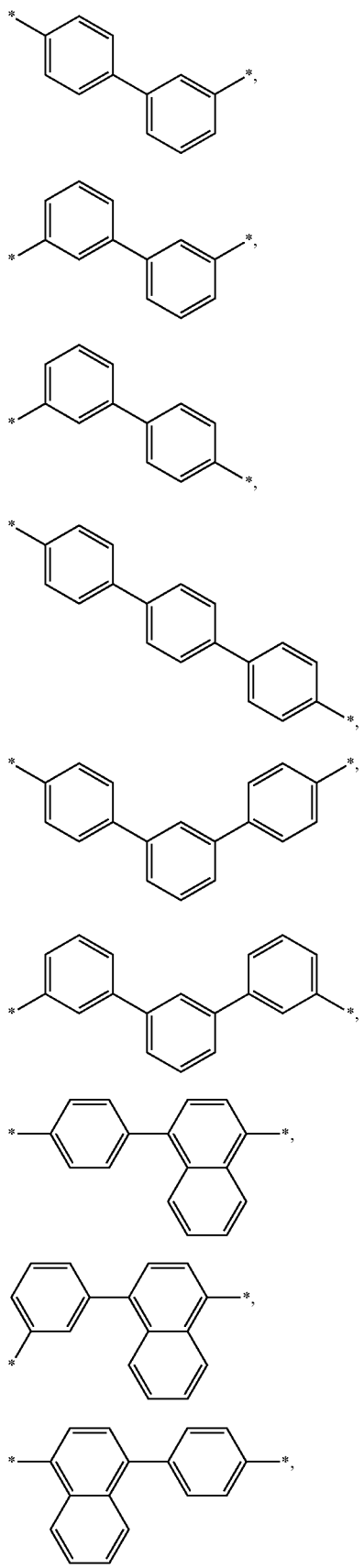

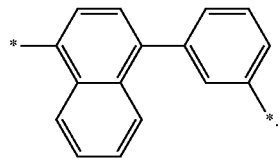

According to one embodiment of the compound according to formula 1, wherein L is selected from C1 to C13, preferably L is selected from C1 to C9, more preferred L is selected from C2, C4 to C6 and C8 to C9, most preferred L is selected from C2.

According to one embodiment of the compound according to formula 1, wherein L is selected from C2 and C4 to C6, preferably C2 and C5.

According to one embodiment, wherein $Ar^2$ of the compound of formula 1 may be selected from D1 to D22:

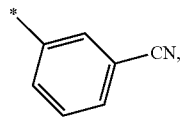

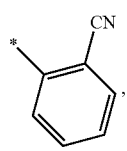

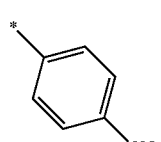

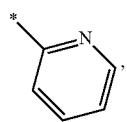

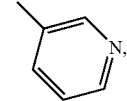

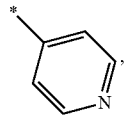

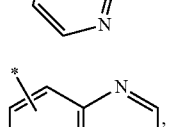

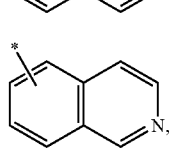

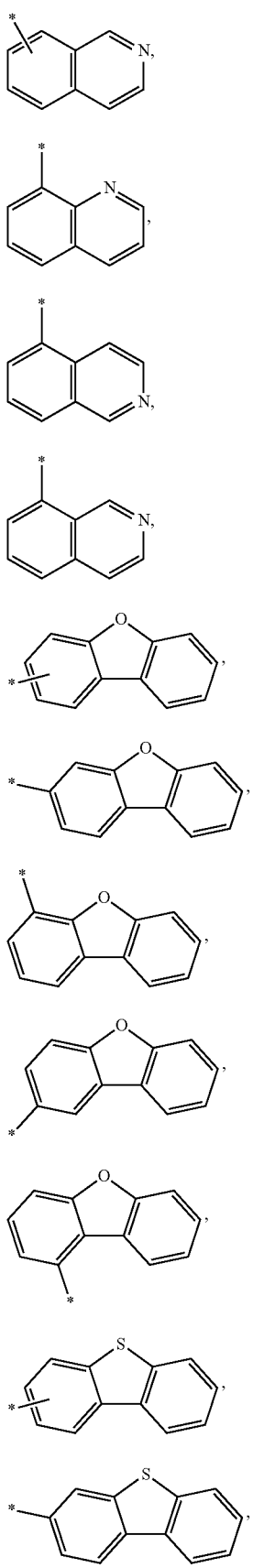
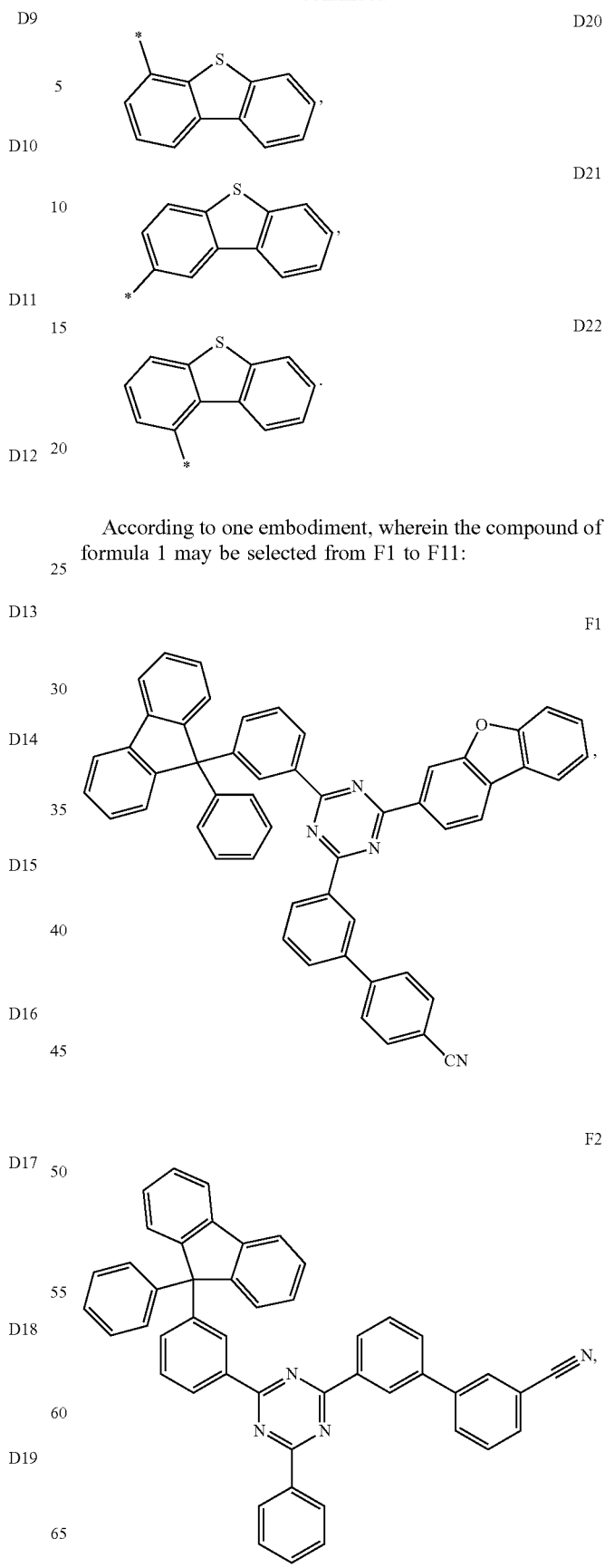
According to one embodiment, wherein the compound of formula 1 may be selected from F1 to F11:

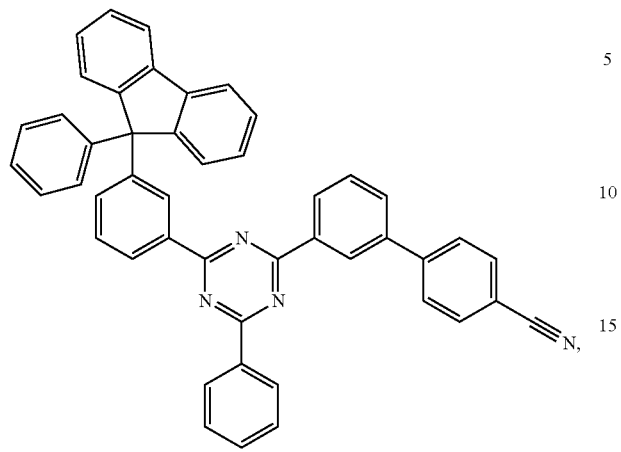
F3
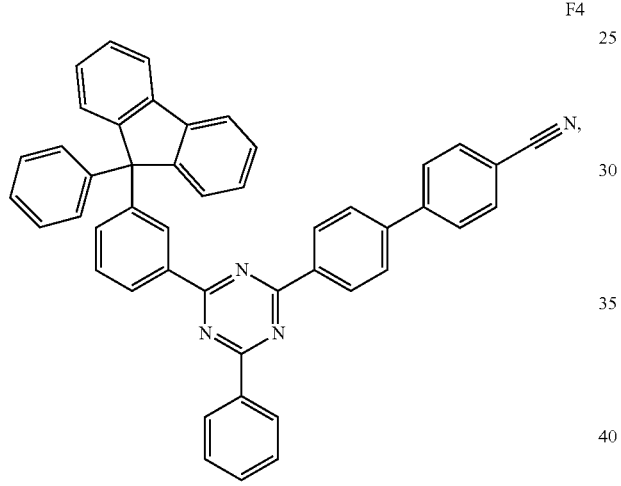
F4
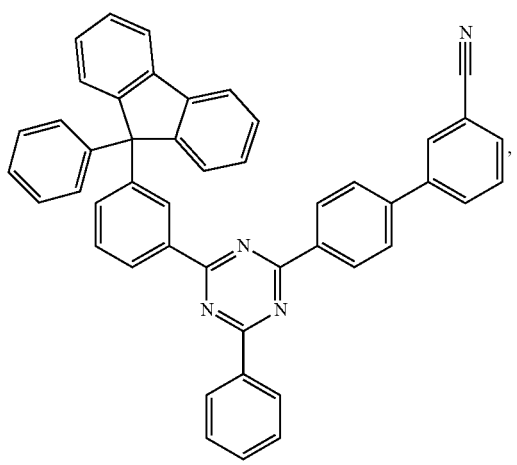
F5
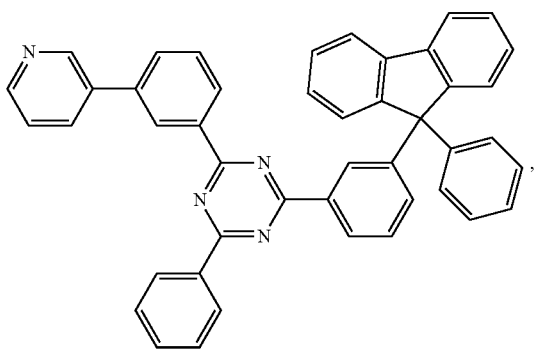
F6
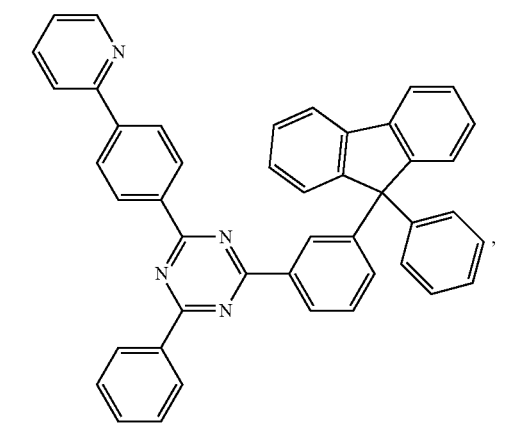
F7
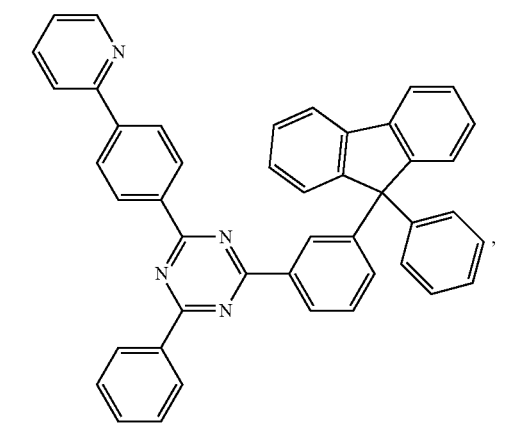
F8
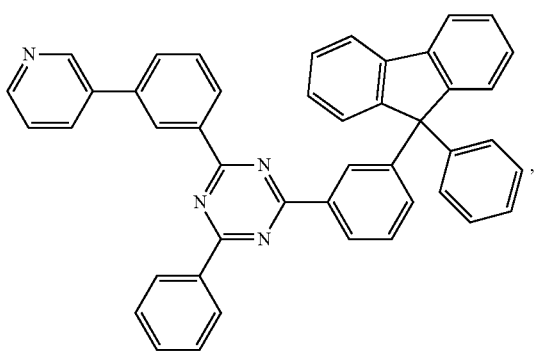
F9

-continued

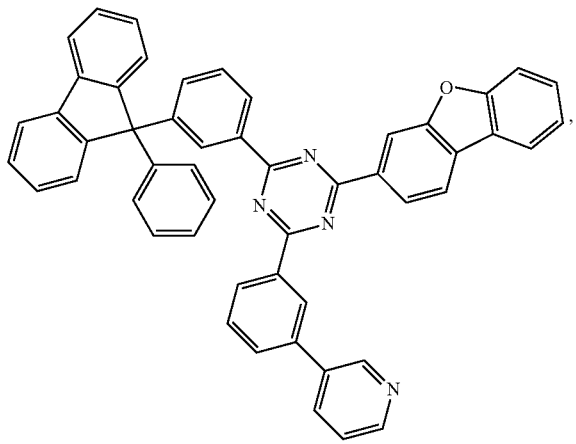

F10

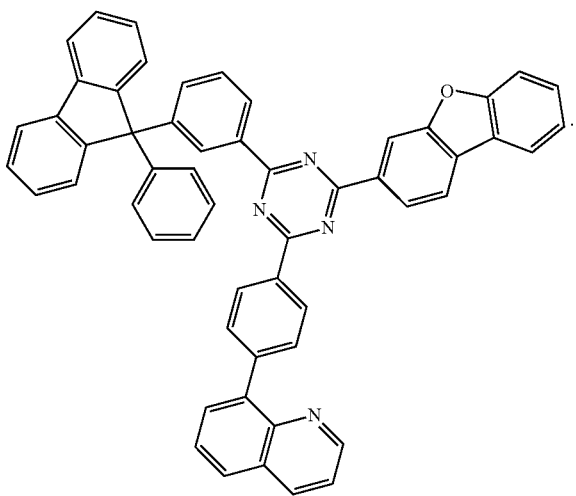

F11

Anode

A material for the anode may be a metal or a metal oxide, or an organic material, preferably a material with work function above about 4.8 eV, more preferably above about 5.1 eV, most preferably above about 5.3 eV. Preferred metals are noble metals like Pt, Au or Ag, preferred metal oxides are transparent metal oxides like ITO or IZO which may be advantageously used in bottom-emitting OLEDs having a reflective cathode.

In devices comprising a transparent metal oxide anode or a reflective metal anode, the anode may have a thickness from about 50 nm to about 100 nm, whereas semitransparent metal anodes may be as thin as from about 5 nm to about 15 nm, and non-transparent metal anodes may have a thickness from about 15 nm to about 150 nm.

Hole Injection Layer (HIL

The hole injection layer may improve interface properties between the anode and an organic material used for the hole transport layer, and is applied on a non-planarized anode and thus may planarize the surface of the anode. For example, the hole injection layer may include a material having a median value of the energy level of its highest occupied molecular orbital (HOMO) between the work function of the anode material and the energy level of the HOMO of the hole transport layer, in order to adjust a difference between the work function of the anode and the energy level of the HOMO of the hole transport layer.

When the hole transport region comprises a hole injection layer 36, the hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

The hole injection layer may further comprise a p-dopant to improve conductivity and/or hole injection from the anode.

p-Dopant

In another aspect, the p-dopant may be homogeneously dispersed in the hole injection layer.

In another aspect, the p-dopant may be present in the hole injection layer in a higher concentration closer to the anode and in a lower concentration closer to the cathode.

The p-dopant may be one of a quinone derivative or a radialene compound but not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), 4,4',4''-((1E,1'E,1''E)-cyclopropane-1,2,3-triylidenetris(cya-nomethanylylidene))-tris(2,3,5,6-tetrafluorobenzonitrile).

Hole Transport Layer (HTL)

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport part of the charge transport region comprises the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in operating voltage.

Hole transport matrix materials used in the hole transport region are not particularly limited. Preferred are covalent compounds comprising a conjugated system of at least 6 delocalized electrons, preferably organic compounds comprising at least one aromatic ring, more preferably organic compounds comprising at least two aromatic rings, even more preferably organic compounds comprising at least three aromatic rings, most preferably organic compounds comprising at least four aromatic rings. Typical examples of hole transport matrix materials which are widely used in hole transport layers are polycyclic aromatic hydrocarbons, triarylene amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

Buffer Layer

The hole transport part of the charge transport region may further include a buffer layer.

Buffer layer that can be suitable used are disclosed in U.S. Pat. Nos. 6,140,763, 6,614,176 and in US2016/248022.

The buffer layer may compensate for an optical resonance distance of light according to a wavelength of the light emitted from the EML, and thus may increase efficiency.

Emission Layer (EML)

The emission layer may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

A thickness of the emission layer may be about 100 Å to about 1000 Å, for example about 200 Å to about 600 Å. When the thickness of the emission layer is within these ranges, the emission layer may have improved emission characteristics without a substantial increase in a operating voltage.

Emitter Host

According to another embodiment, the emission layer comprises compound of formula 1 as emitter host.

The emitter host compound has at least three aromatic rings, which are independently selected from carbocyclic rings and heterocyclic rings.

Other compounds that can be used as the emitter host is an anthracene matrix compound represented by formula 400 below:

Formula 400

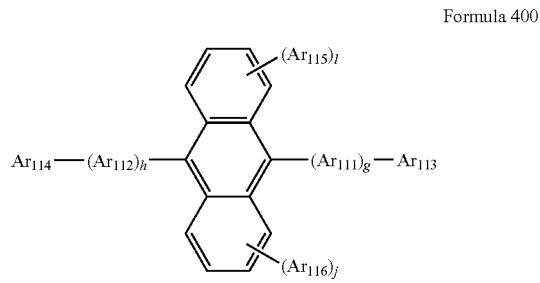

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ arylene group; and g, h, i, and j may be each independently an integer from 0 to 4.

In some embodiments, $Ar_{111}$ and $Ar_{112}$ in formula 400 may be each independently one of a phenylene group, a naphthalene group, a phenanthrenylene group, or a pyrenylene group; or a phenylene group, a naphthalene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of a $C_1$-$C_{10}$ alkyl group substituted with at least one of a phenyl group, a naphthyl group, or an anthryl group;

a phenyl group, a naphthyl group, an anthryl group, a pyrenyl group, a phenanthrenyl group, or a fluorenyl group;

a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group

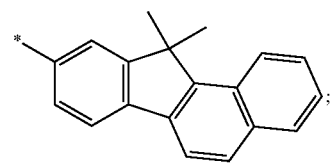 [SMILES: *c1ccc2c(c1)C(C)(C)c1c-2ccc2ccccc12]

or formulas 7 or 8

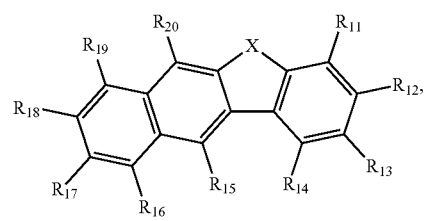

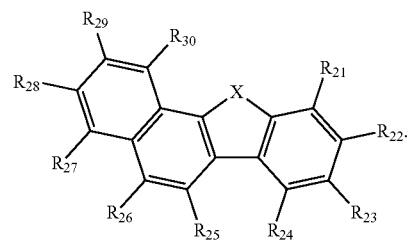

Wherein in the formulas 7 and 8, X is selected form an oxygen atom and a sulfur atom, but embodiments of the invention are not limited thereto.

In the formula 7, any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula 8, any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

Emitter Dopant

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The emitter may be a red, green, or blue emitter.

The dopant may be a fluorescent dopant, for example ter-fluorene, the structures are shown below. 4,4'-bis(4-diphenyl aminostyryl)biphenyl (DPAVBI, 2,5,8,11-tetra-tert-butyl perylene (TBPe), and Compound 8 below are examples of fluorescent blue dopants.

Compound 8

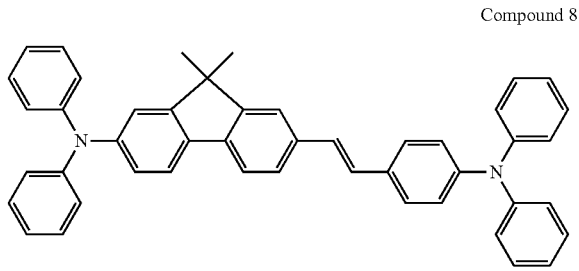 [SMILES: CC1(C)c2cc(/C=C/c3ccc(N(c4ccccc4)c4ccccc4)cc3)ccc2-c2ccc(N(c3ccccc3)c3ccccc3)cc21]

The dopant may be a phosphorescent dopant, and examples of the phosphorescent dopant may be an organic metal compound comprising Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

$$J_2MX \qquad (Z).$$

In formula Z, M is a metal, and J and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the J and X may be, for example a bidendate ligand.

Electron Transport Layer (ETL)

According to another embodiment, the organic semiconductor layer that comprises a compound of formula 1 is an electron transport layer. In another embodiment the electron transport layer may consist of a compound of formula 1.

For example, an organic light emitting diode according to an embodiment of the present invention comprises at least one electron transport layer, and in this case, the electron transport layer comprises a compound of formula 1, or preferably of at least one compound of formulae F1 to F11.

In another embodiment, the organic electronic device comprises an electron transport region of a stack of organic layers formed by two or more electron transport layers, wherein at least one electron transport layer comprises a compound of formula 1.

The electron transport layer may include one or two or more different electron transport compounds.

According to another embodiment, a second electron transport layer comprises at least one compound of formula 1 according to the invention and a first electron transport layer comprises a matrix compound, which is selected different to the compound of formula 1 according to the invention, and may be selected from:

an anthracene based compound or a hetero substituted anthracene based compound, preferably 2-(4-(9,10-di(naphthalen-2-yl)anthracene-2-yl)phenyl)-1-phenyl-1H-benzo[d]imidazole and/or N4,N4''-di(naphthalen-1-yl)-N4,N4''-diphenyl-[1,1':4',1''-terphenyl]-4,4''-diamine.

According to another embodiment, a first electron transport layer comprises at least one compound of formula 1 according to the invention and a second electron transport layer comprises a matrix compound, which is selected different to the compound of formula 1 according to the invention, and may be selected from:

a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide; or a substituted phenanthroline compound, preferably 2,4,7,9-tetraphenyl-1,10-phenanthroline or 2,9-di(biphenyl-4-yl)-4,7-diphenyl-1,10-phenanthroline.

According to another embodiment a first electron transport layer comprises at least one compound of formula 1 according to the invention and a second electron transport layer comprises a matrix compound, which is selected different to the compound of formula 1 according to the invention, and may be selected from a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide.

According to another embodiment, a first and a second electron transport layers comprise a compound of formula 1, wherein the compound of formula 1 is not selected the same.

The thickness of the first electron transport layer may be from about 0.5 nm to about 100 nm, for example about 2 nm to about 40 nm. When the thickness of the first electron transport layer is within these ranges, the first electron transport layer may have improved electron transport ability without a substantial increase in operating voltage.

A thickness of an optional second electron transport layer may be about 1 nm to about 100 nm, for example about 2 nm to about 20 nm. When the thickness of the electron transport layer is within these ranges, the electron transport layer may have satisfactory electron transporting ability without a substantial increase in operating voltage.

The electron transport layer may further comprise an alkali halide and/or alkali organic complex.

According to another embodiment, the first and second electron transport layers comprise a compound of formula 1, wherein the second electron transport layer further comprises an alkali halide and/or alkali organic complex.

Alkali Halide

Alkali halides, also known as alkali metal halides, are the family of inorganic compounds with the chemical formula MX, where M is an alkali metal and X is a halogen.

M can be selected from Li, Na, Potassium, Rubidium and Cesium.

X can be selected from F, Cl, Br and J.

According to various embodiments of the present invention a lithium halide may be preferred. The lithium halide can be selected from the group comprising LiF, LiCl, LiBr and LiJ. However, most preferred is LiF.

The alkali halide is essentially non-emissive or non-emissive.

Alkali Organic Complex

The alkali organic complex comprises an alkali metal and at least one organic ligand. The alkali metal is preferably selected from lithium.

According to various embodiments of the present invention the organic ligand of the lithium organic complex is a quinolate, a borate, a phenolate, a pyridinolate or a Schiff base ligand;

preferably the lithium quinolate complex has the formula III, IV or V:

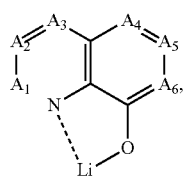
(III)

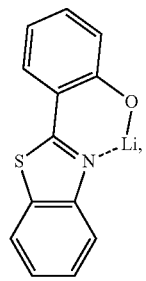
(IV)

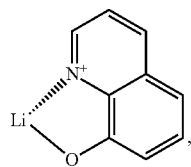
(V)

wherein
- $A_1$ to $A_6$ are same or independently selected from CH, CR, N and O;
- R is same or independently selected from hydrogen, halogen, alkyl or arylene or heteroarylene with 1 to 20 carbon atoms; and more preferred A1 to A6 are CH;
- preferably the borate based organic ligand is a tetra(1H-pyrazol-1-yl)borate;
- preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;
- preferably the pyridinolate is a 2-(diphenylphosphoryl)pyridin-3-olate.

According to various embodiments of the present invention the organic ligand of the alkali organic complex, preferably of a lithium organic complex, can be a quinolate. Quinolates that can be suitable used are disclosed in WO 2013079217 A1 and incorporated by reference.

According to various embodiments of the present invention the organic ligand of the lithium organic complex can be a borate based organic ligand, Preferably the lithium organic complex is a lithium tetra(1H-pyrazol-1-yl)borate. Borate based organic ligands that can be suitable used are disclosed in WO 2013079676 A1 and incorporated by reference.

According to various embodiments of the present invention the organic ligand of the lithium organic complex can be a phenolate ligand, Preferably the lithium organic complex is a lithium 2-(diphenylphosphoryl)phenolate. Phenolate ligands that can be suitable used are disclosed in WO 2013079678 A1 and incorporated by reference.

Further, phenolate ligands can be selected from the group of pyridinolate, preferably 2-(diphenylphosphoryl)pyridin-3-olate. Pyridine phenolate ligands that can be suitable used are disclosed in JP 2008195623 and incorporated by reference.

In addition, phenolate ligands can be selected from the group of imidazol phenolates, preferably 2-(1-phenyl-1H-benzo[d]imidazol-2-yl)phenolate. Imidazol phenolate ligands that can be suitable used are disclosed in JP 2001291593 and incorporated by reference.

Also, phenolate ligands can be selected from the group of oxazol phenolates, preferably 2-(benzo[d]oxazol-2-yl)phenolate. Oxazol phenolate ligands that can be suitable used are disclosed in US 20030165711 and incorporated by reference.

The alkali organic complex may be essentially non-emissive.

n-Dopant

According to various embodiments, the organic semiconductor layer comprising a compound of formula 1 may further comprise an n-dopant.

Electrically neutral metal complexes suitable as n-dopants may be e.g. strongly reductive complexes of some transition metals in low oxidation state. Particularly strong n-dopants may be selected for example from Cr(II), Mo(II) and/or W(II) guanidinate complexes such as $W_2(hpp)_4$, as described in more detail in WO2005/086251.

Electrically neutral organic radicals suitable as n-dopants may be e.g. organic radicals created by supply of additional energy from their stable dimers, oligomers or polymers, as described in more detail in EP 1 837 926 B1, WO2007/107306, or WO2007/107356. Specific examples of such suitable radicals may be diazolyl radicals, oxazolyl radicals and/or thiazolyl radicals.

In another embodiment, the organic semiconductor layer may further comprise an elemental metal. An elemental metal is a metal in a state of metal in its elemental form, a metal alloy, or a metal cluster. It is understood that metals deposited by vacuum thermal evaporation from a metallic phase, e.g. from a bulk metal, vaporize in their elemental form. It is further understood that if the vaporized elemental metal is deposited together with a covalent matrix, the metal atoms and/or clusters are embedded in the covalent matrix. In other words, it is understood that any metal doped covalent material prepared by vacuum thermal evaporation contains the metal at least partially in its elemental form.

For the use in consumer electronics, only metals containing stable nuclides or nuclides having very long halftime of radioactive decay might be applicable. As an acceptable level of nuclear stability, the nuclear stability of natural potassium can be taken.

In one embodiment, the n-dopant is selected from electropositive metals selected from alkali metals, alkaline earth metals, rare earth metals and metals of the first transition period Ti, V, Cr and Mn. Preferably, the n-dopant is selected from Li, Na, K, Rb, Cs, Mg, Ca, Sr, Ba, Sm, Eu, Tm, Yb; more preferably from Li, Na, K, Rb, Cs, Mg and Yb, even more preferably from Li, Na, Cs and Yb, most preferably from Li, Na and Yb.

The n-dopant may be essentially non-emissive.

Electron Injection Layer (EIL)

According to another aspect of the invention, the organic electroluminescent device may further comprise an electron injection layer between the electron transport layer (first-ETL) and the cathode.

The electron injection layer (EIL) may facilitate injection of electrons from the cathode.

According to another aspect of the invention, the electron injection layer comprises:
(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or
(ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer (second-ETL) is identical with the alkali metal salt and/or complex of the injection layer.

The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in operating voltage.

The electron injection layer may comprise a compound of formula 1.

Cathode

A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al—Li), calcium (Ca), magnesium-indium (Mg—In), magnesium-silver (Mg—Ag), silver (Ag) etc. In order to manufacture a top-emission light-emitting device having a reflective anode deposited on a substrate, the cathode may be formed as a light-transmissive electrode from, for example, indium tin oxide (ITO), indium zinc oxide (IZO) or silver (Ag).

In devices comprising a transparent metal oxide cathode or a reflective metal cathode, the cathode may have a thickness from about 50 nm to about 100 nm, whereas semitransparent metal cathodes may be as thin as from about 5 nm to about 15 nm.

Substrate

A substrate may be further disposed under the anode or on the cathode. The substrate may be a substrate that is used in a general organic light emitting diode and may be a glass substrate or a transparent plastic substrate with strong mechanical strength, thermal stability, transparency, surface smoothness, ease of handling, and water resistance.

Hereinafter, the embodiments are illustrated in more detail with reference to examples. However, the present disclosure is not limited to the following examples.

DESCRIPTION OF THE DRAWINGS

These and/or other aspects and advantages of the present invention will become apparent and more readily appreciated from the following description of the exemplary embodiments, taken in conjunction with the accompanying drawings, of which.

Figure 1:
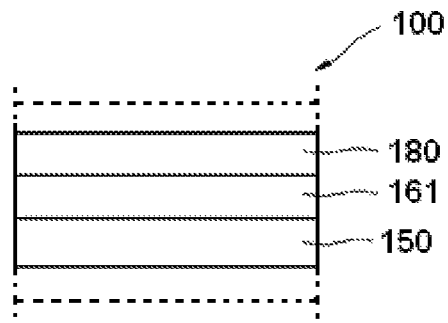
FIG. 1 is a schematic sectional view of an organic light-emitting diode (OLED), according to an exemplary embodiment of the present invention with an emission layer, one electron transport layer and an electron injection layer.

Reference will now be made in detail to the exemplary aspects, examples of which are illustrated in the accompanying drawings, wherein like reference numerals refer to the like elements throughout. The exemplary embodiments are described below, in order to explain the aspects, by referring to the figures.

Herein, when a first element is referred to as being formed or disposed "on" a second element, the first element can be disposed directly on the second element, or one or more other elements may be disposed there between. When a first element is referred to as being formed or disposed "directly on" a second element, no other elements are disposed there between.

The term "contacting sandwiched" refers to an arrangement of three layers whereby the layer in the middle is in direct contact with the two adjacent layers.

The organic light emitting diodes according to an embodiment of the present invention may include a hole transport region; an emission layer; and a first electron transport layer comprising a compound according to formula 1.

FIG. 1 is a schematic sectional view of an organic light-emitting diode 100, according to an exemplary embodiment of the present invention. The OLED 100 comprises an emission layer 150, an electron transport layer (ETL) 161 comprising a compound of formula 1 and an electron injection layer 180, whereby the first electron transport layer 161 is disposed directly on the emission layer 150 and the electron injection layer 180 is disposed directly on the first electron transport layer 161.

Figure 2:
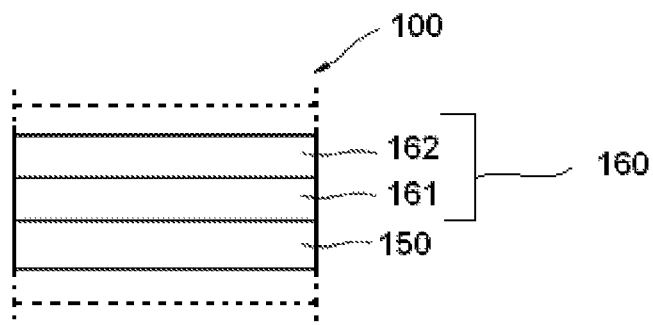
FIG. 2 is a schematic sectional view of an organic light-emitting diode (OLED), according to an exemplary embodiment of the present invention with an emission layer and two electron transport layers.

FIG. 2 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 comprising a compound of formula 1 and a second electron transport layer 162, whereby the second electron transport layer 162 is disposed directly on the first electron transport layer 161. Alternatively. the electron transport layer stack (ETL) 160 comprises a first electron transport layer 161 and a second electron transport layer 162 comprising compound of formula 1, whereby the second electron transport layer 162 is disposed directly on the first electron transport layer 161.

Figure 3:
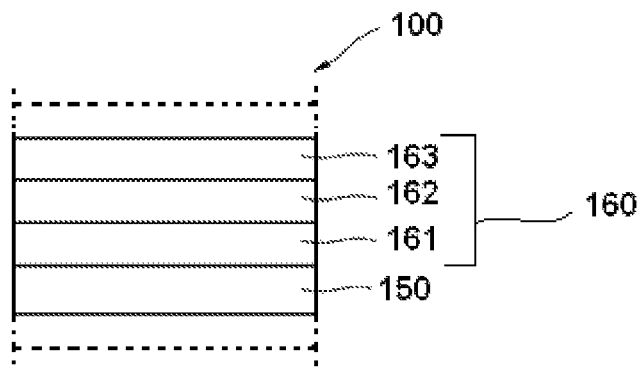
FIG. 3 is a schematic sectional view of an OLED, according to an exemplary embodiment of the present invention with an emission layer and three electron transport layers.

FIG. 3 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 that comprises a compound of formula 1, a second electron transport layer 162 that comprises a compound of formula 1 but different to the compound of the first electron transport layer, and a third electron transport layer 163, whereby the second electron transport layer 162 is disposed directly on the first electron transport layer 161 and the third electron transport layer 163 is disposed directly on the first electron transport layer 162.

Figure 4:
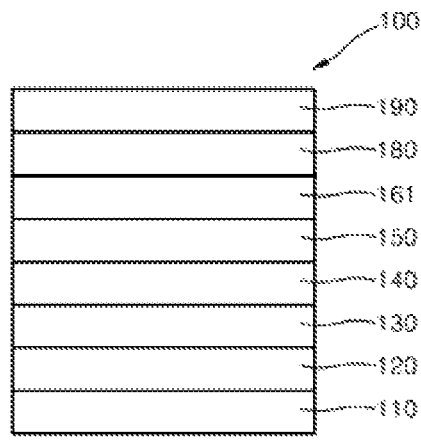
FIG. 4 is a schematic sectional view of an organic light-emitting diode (OLED), according to an exemplary embodiment of the present invention with an emission layer and one electron transport layer.

FIG. 4 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, one first electron transport layer (ETL) 161, an electron injection layer (EIL) 180, and a cathode electrode 190. The first electron transport layer (ETL) 161 comprises a compound of formula 1 and optionally an alkali halide or alkali organic complex. The electron transport layer (ETL) 161 is formed directly on the EML 150.

Figure 5:
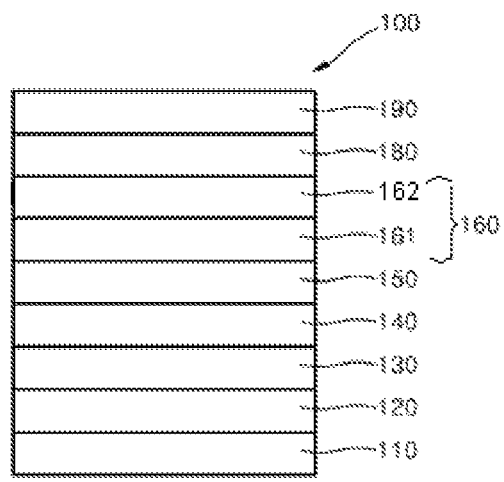
FIG. 5 is a schematic sectional view of an organic light-emitting diode (OLED), according to an exemplary embodiment of the present invention with an emission layer and two electron transport layers.

FIG. 5 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a cathode electrode 190. The electron transport layer (ETL) 160 comprises a first electron transport layer 161 and a second electron transport layer 162, wherein the first electron transport layer is arranged near to the anode (120) and the second electron transport layer is arranged near to the cathode (190). The first and/or the second electron transport layer comprise a compound of formula 1 and optionally an alkali halide or alkali organic complex.

Figure 6:
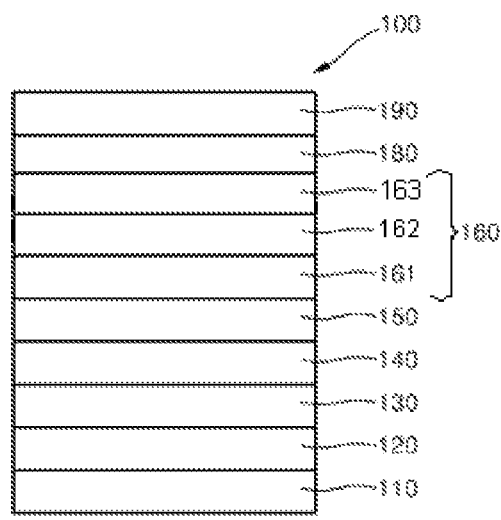
FIG. 6 is a schematic sectional view of an OLED, according to an exemplary embodiment of the present invention with an emission layer and three electron transport layers.

FIG. 6 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a second cathode electrode 190. The electron transport layer stack (ETL) 160 comprises a first electron transport layer 161, a second electron transport layer 162 and a third electron transport layer 163. The first electron transport layer 161 is formed directly on the emission layer (EML) 150. The first, second and/or third electron transport layer comprise a compound of formula 1 that is different for each layer, and optionally an alkali halide or alkali organic complex.

Organic Semiconductor Layer

According to another aspect an organic semiconductor layer may comprises at least one compound of formula 1.

According to one embodiment the organic semiconductor layer may comprises at least one compound of formula 1 and further comprises a metal, metal salt or organic alkali metal complex, preferably alkali metal complex, more preferably LiQ or alkali borate.

According to one embodiment, wherein at least one organic semiconductor layer is arranged between the emission layer and the cathode, preferably between the auxiliary electron transport layer and the cathode.

In another embodiment, the organic semiconductor layer is arranged between the emission layer and the electron transport layer.

According to one embodiment, the organic semiconductor layer is arranged between the first and second emission layer. The organic semiconductor layer can be an electron transport layer, an emission layer, a hole blocking layer, a charge generation layer and/or an electron injection layer, preferably an electron transport layer or a charge generation layer, and more preferred an electron transport layer.

According to one embodiment, the organic semiconductor layer can be arranged between a photoactive layer and a cathode layer, preferably between an emission layer or light-absorbing layer and the cathode layer, preferably the organic semiconductor layer is an electron transport layer.

According to one embodiment, the organic semiconductor layer may comprise at least one alkali halide or alkali organic complex.

An organic semiconductor layer comprises a compound according to formula 1 is essentially non-emissive or non-emitting.

Organic Electronic Device

According to another embodiment it is an organic electronic device provided comprising an organic semiconductor layer according to the present invention.

An organic electronic device according to the invention comprises at least one organic semiconductor layer, wherein at least one organic semiconductor layer comprises a compound according to formula 1.

An organic electronic device according to one embodiment, which comprises at least one organic semiconductor layer that comprises a compound according to formula 1, wherein this layer is essentially non-emissive or non-emitting.

According to one embodiment, the organic electronic device may comprises at least one organic semiconductor layer, wherein the organic semiconductor layer can be an electron transport layer, a hole blocking layer, an n-type charge generation layer or an electron injection layer, preferably an electron transport layer or an n-type charge generation layer, more preferred an electron transport layer.

According to one embodiment the organic electronic device comprises at least one organic semiconductor layer that can be arranged between a photoactive layer and a cathode layer, preferably between an emission layer or light-absorbing layer and the cathode layer, preferably the organic semiconductor layer is an electron transport layer.

According to one embodiment the organic electronic device comprises at least one organic semiconductor layer, wherein at least one organic semiconductor layer is arranged between the emission layer and the cathode, preferably between the auxiliary electron transport layer and the cathode.

According to one embodiment the organic electronic device comprises at least one anode layer, at least one cathode layer and at least one emission layer, wherein the organic semiconductor layer is preferably arranged between the emission layer and the cathode layer.

According to one embodiment, the organic electronic device may comprises at least one organic semiconductor layer comprising a compound of formula 1 that is an electron transport layer, an emission layer, a hole blocking layer, a charge generation layer and/or an electron injection layer, preferably an electron transport layer or a charge generation layer, more preferred an electron transport layer.

An organic electronic device according to one embodiment may include a substrate, an anode layer, an organic semiconductor layer comprising a compound of formula 1, and a cathode layer.

The organic electronic device according to according to one embodiment may comprises at least one organic semiconductor layer, wherein the organic semiconductor layer comprising a compound of formula 1 is arranged between a photoactive layer and a cathode layer, preferably between an emission layer or light-absorbing layer and the cathode layer, preferably the organic semiconductor layer is an electron transport layer.

The organic electronic device according to according to one embodiment may comprises at least one organic semiconductor layer comprising a compound of formula 1, wherein the at least one organic semiconductor layer further comprises at least one alkali halide or alkali organic complex.

An organic electronic device according to one embodiment comprises at least one organic semiconductor layer comprising at least one compound of formula 1, at least one anode layer, at least one cathode layer and at least one emission layer, wherein the organic semiconductor layer comprising at least one compound of formula 1 is preferably arranged between the emission layer and the cathode layer.

An organic electronic device according to one embodiment comprises at least one organic semiconductor layer comprising at least one compound of formula 1 and further comprises at least one alkali halide or alkali organic complex.

An organic electronic device according to one embodiment comprises at least one organic semiconductor layer, at least one anode layer, at least one cathode layer and at least one emission layer, wherein the organic semiconductor layer comprising at least one compound of formula 1 is preferably arranged between the emission layer and the cathode layer. Preferably the at least one organic semiconductor layer is an electron transport layer.

An organic light-emitting diode (OLED) according to the invention may include an anode, a hole transport layer (HTL), an emission layer (EML), an electron transport layer (ETL) comprising at least one compound of formula 1, and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device. A light emitting device can be an OLED.

According to one embodiment the OLED may have the following layer structure, wherein the layers having the following order:
an anode layer, a hole injection layer, optional a first hole transport layer, optional a second hole transport layer, an emission layer, an electron transport layer comprising a compound of formula 1 according to the invention, an electron injection layer, and a cathode layer.

According to another aspect of the present invention, there is provided a method of manufacturing an organic electronic device, the method using:
at least one deposition source, preferably two deposition sources and more preferred at least three deposition sources.

The methods for deposition that can be suitable used comprise:
deposition via vacuum thermal evaporation;
deposition via solution processing, preferably the processing is selected from spin-coating, printing, casting; and/or
slot-die coating.

According to various embodiments of the present invention, there is provided a method using:
a first deposition source to release the compound of formula 1 according to the invention, and
a second deposition source to release the alkali halide or alkali organic complex, preferably a lithium halide or lithium organic complex;
the method comprising the steps of forming the electron transport layer stack; whereby for an organic light-emitting diode (OLED):
the first electron transport layer is formed by releasing the compound of formula 1 according to the invention from the first deposition source and the alkali halide or alkali organic complex, preferably a lithium halide or lithium organic complex from the second deposition source.

According to various embodiments of the present invention, the method may further include forming on the anode electrode an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
on a substrate a first anode electrode is formed,
on the first anode electrode an emission layer is formed,
on the emission layer an electron transport layer stack is formed, preferably a first electron transport layer is formed on the emission layer and optional a second electron transport layer is formed,
and finally a cathode electrode is formed,
optional a hole injection layer, a hole transport layer, and a hole blocking layer, formed in that order between the first anode electrode and the emission layer,
optional an electron injection layer is formed between the electron transport layer and the cathode electrode.

According to various embodiments of the present invention, the method may further include forming an electron injection layer on a first electron transport layer. However, according to various embodiments of the OLED of the present invention, the OLED may not comprise an electron injection layer.

According to various embodiments, the OLED may have the following layer structure, wherein the layers having the following order:
an anode, first hole transport layer, second hole transport layer, emission layer, optional second electron transport layer, first electron transport layer comprising a compound of formula 1 according to the invention, optional an electron injection layer, and a cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the embodiments are illustrated in more detail with reference to examples. However, the present disclosure is not limited to the following examples. Reference will now be made in detail to the exemplary aspects.

Preparation of Compounds of Formula 1

Compounds of formula 1 may be synthesized as described below.

Synthesis of compounds of formula 1 with Ar²=pyridyl:

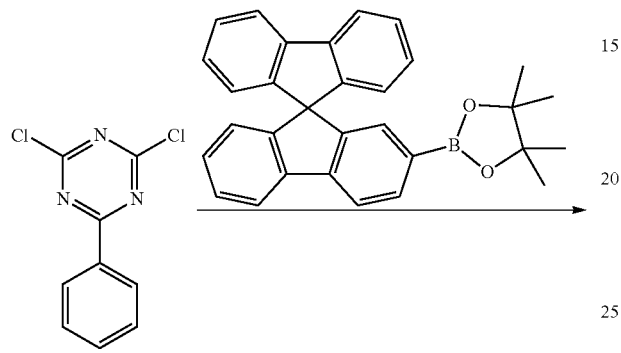

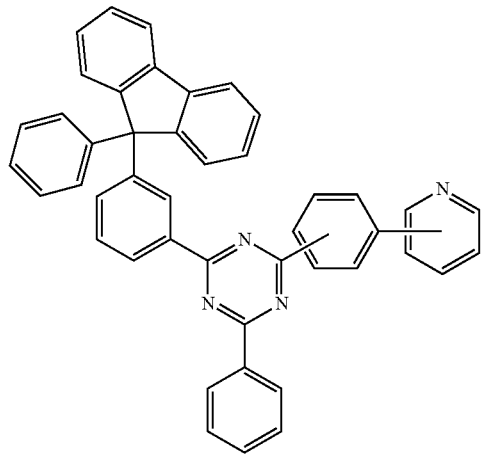

2-chloro-4-phenyl-6-(3-(9-phenyl-9H-fluoren-9-yl)phenyl)-1,3,5-triazine

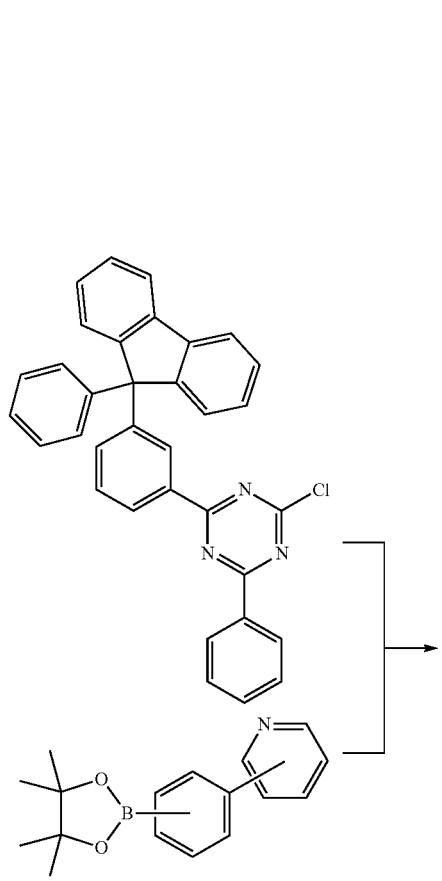

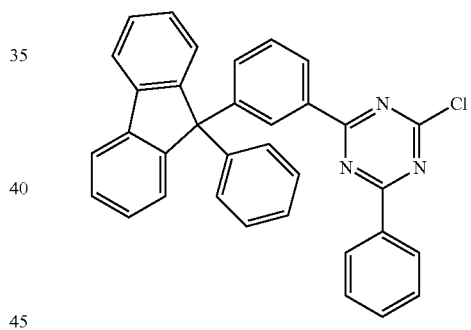

A flask was flushed with nitrogen and charged with 2,4-dichloro-6-phenyl-1,3,5-triazine (18.0 g, 79.4 mmol), 4,4,5,5-tetramethyl-2-(3-(9-phenyl-9H-fluoren-9-yl)phenyl)-1,3,2-dioxaborolane (30 g, 67.5 mol), Pd(PPh₃)₄ (4.6 g, 3.98 mmol), and K₂CO₃ (27.5 g, 199 mmol). A mixture of deaerated toluene/THF/water (1:1:1, 660 mL) was added and the reaction mixture was heated to 65° C. under a nitrogen atmosphere for 6 h. Subsequently, all volatiles have been removed in vacuo, the residue was suspended in dichloromethane and washed with water three times. After drying over MgSO₄, the organic phase was concentrated to a minimal amount and precipitation was induced by addition of acetonitrile. The precipitate was collected by suction filtration and washed with additional acetonitrile. Further purification was achieved by trituration with hot ethyl acetate to yield 10 g (30%) of an off-white solid after drying. m/z=508 ([M]⁺).

2-phenyl-4-(3-(9-phenyl-9H-fluoren-9-yl)phenyl)-6-(3-(pyridin-3-yl)phenyl)-1,3,5-triazine

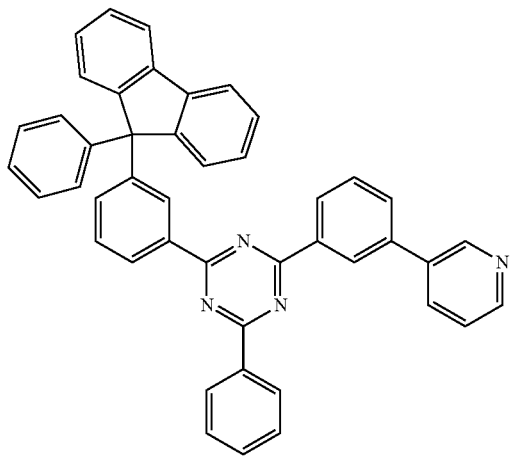 [SMILES: c1ccc(-c2nc(-c3cccc(-c4cccnc4)c3)nc(-c3cccc(C4(c5ccccc5)c5ccccc5-c5ccccc54)c3)n2)cc1]

A flask was flushed with nitrogen and charged with 2-chloro-4-phenyl-6-(3-(9-phenyl-9H-fluoren-9-yl)phenyl)-1,3,5-triazine (7.3 g, 14.37 mmol), 3-(3-(4,4,5,5-tetramethyl-1,3,2-dioxaborolan-2-yl)phenyl)pyridine (4.5 g, 16.01 mmol), Pd(PPh$_3$)$_4$ (0.34 g, 0.3 mmol), and K$_2$CO$_3$ (4.1 g, 29.5 mmol). A mixture of deaerated THF/water (5:1, 90 mL) was added and the reaction mixture was heated to reflux under a nitrogen atmosphere for 22 h. After cooling down to room temperature, the THF was removed in vacuo, dichloromethane and water were added and the phases were separated. The organic phase was washed with aq. sodium diethylcarbamodithioate and brine, dried over MgSO$_4$, filtered and evaporated to dryness. Purification was achieved by repeated column chromatography (silica, n-hexane/chloroform 1:1 to n-hexane/chloroform/ethyl acetate 3:3:1) followed by recrystallization from cyclohexane to yield 3.5 g (39%) of a white solid after drying. Final purification was achieved by sublimation. m/z=627 ([M+H]$^+$).

2-phenyl-4-(3-(9-phenyl-9H-fluoren-9-yl)phenyl)-6-(4-(pyridin-2-yl)phenyl)-1,3,5-triazine

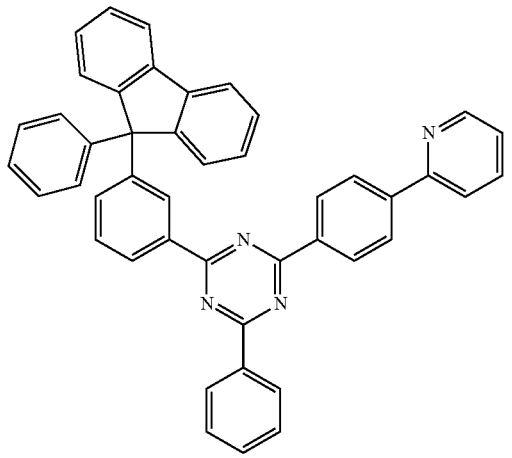 [SMILES: c1ccc(-c2nc(-c3ccc(-c4ccccn4)cc3)nc(-c3cccc(C4(c5ccccc5)c5ccccc5-c5ccccc54)c3)n2)cc1]

A flask was flushed with nitrogen and charged with 2-chloro-4-phenyl-6-(3-(9-phenyl-9H-fluoren-9-yl)phenyl)-1,3,5-triazine (7.4 g, 14.6 mmol), 2-(4-(4,4,5,5-tetramethyl-1,3,2-dioxaborolan-2-yl)phenyl)pyridine (4.71 g, 16.75 mmol), Pd(PPh$_3$)$_4$ (0.34 g, 0.29 mmol), and K$_2$CO$_3$ (4.03 g, 29 mmol). A mixture of deaerated THF/water (2:1, 90 mL) was added and the reaction mixture was heated to reflux under a nitrogen atmosphere for 23 h. After cooling down to 5° C., the resulting precipitate was isolated by suction filtration and washed with THF and n-hexane. The obtained white solid was dissolved in chloroform and washed with water three times. After drying over MgSO$_4$, the organic phase was filtered over a pad of Florisil. After rinsing with additional chloroform, the colorless filtrate was concentrated in vacuo to a minimal volume and n-hexane was added. After stirring for 30 min., the resulting white precipitate was isolated by suction filtration and washed with n-hexane. Further purification was achieved by column chromatography (silica, chloroform to chloroform/methanol 99:1) to yield 6.8 g (75%) of a white solid after drying. Final purification was achieved by sublimation. m/z=627 ([M+H]$^+$).

Synthesis of Compounds of Formula 1 with Ar$^2$=C$_6$H$_5$CN:

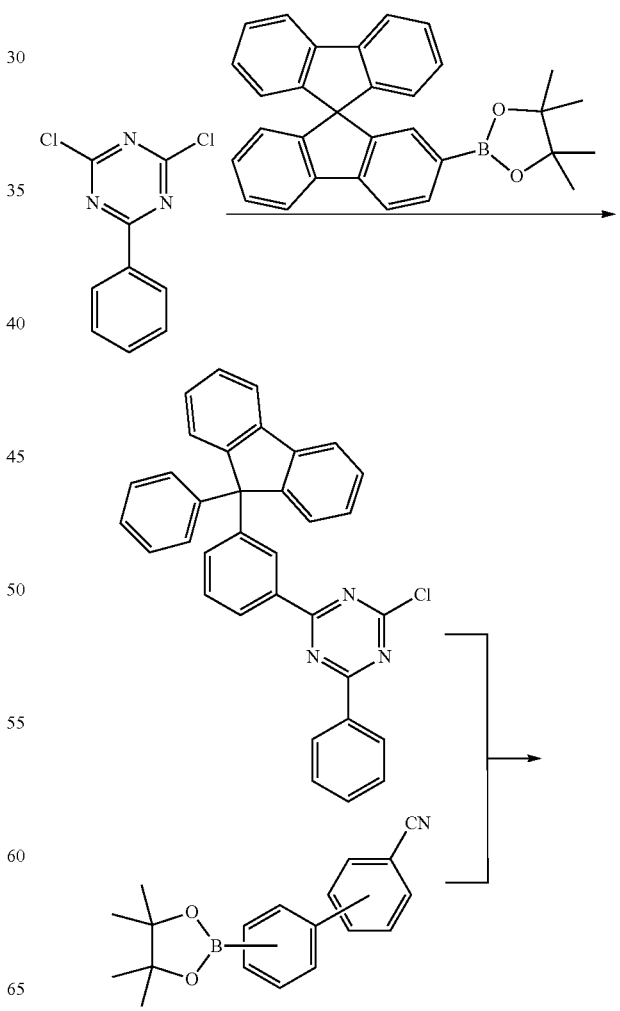

-continued

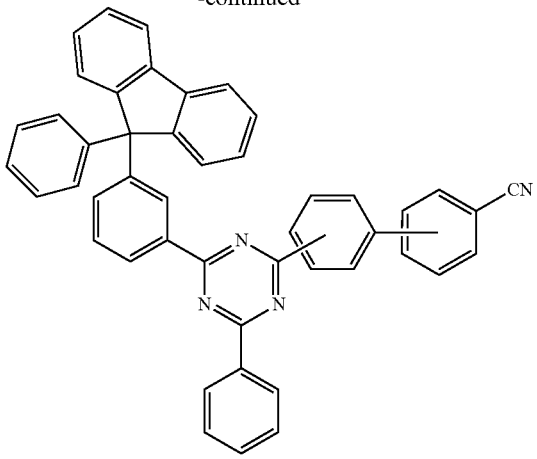

3'-(4-phenyl-6-(3-(9-phenyl-9H-fluoren-9-yl)phenyl)-1,3,5-triazin-2-yl)-[1,1'-biphenyl]-3-carbonitrile

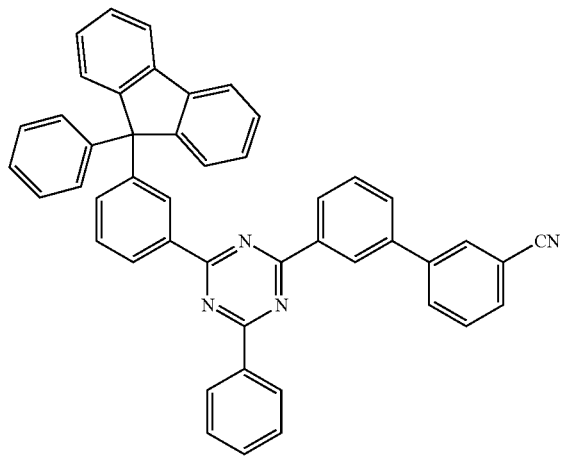 [SMILES: N#Cc1cccc(-c2cccc(-c3nc(-c4ccccc4)nc(-c4cccc(C5(c6ccccc6)c6ccccc6-c6ccccc65)c4)n3)c2)c1]

A flask was flushed with nitrogen and charged with 2-chloro-4-phenyl-6-(3-(9-phenyl-9H-fluoren-9-yl)phenyl)-1,3,5-triazine (14.27 g, 28.1 mmol), 3'-(4,4,5,5-tetramethyl-1,3,2-dioxaborolan-2-yl)-[1,1'-biphenyl]-3-carbonitrile (9.0 g, 29.5 mmol), Pd(PPh$_3$)$_4$ (0.65 g, 0.56 mmol), and K$_2$CO$_3$ (7.76 g, 56 mmol). A mixture of deaerated THF/water (2:1, 135 mL) was added and the reaction mixture was heated to reflux under a nitrogen atmosphere for 23 h. After cooling down to room temperature, the THF was removed in vacuo, dichloromethane was added and the organic phase was washed with water four times. Subsequently, the organic phase was dried over MgSO$_4$ and filtered over a pad of Florisil. After rinsing with additional dichloromethane, the colorless filtrate was evaporated to dryness. Further purification was achieved by column chromatography (silica, toluene/n-hexane 1:1 to toluene/n-hexane 3:1) to yield 17.7 g (97%) of a white solid after drying. Final purification was achieved by sublimation. m/z=651 ([M+H]$^+$).

3'-(4-phenyl-6-(3-(9-phenyl-9H-fluoren-9-yl)phenyl)-1,3,5-triazin-2-yl)-[1,1'-biphenyl]-4-carbonitrile

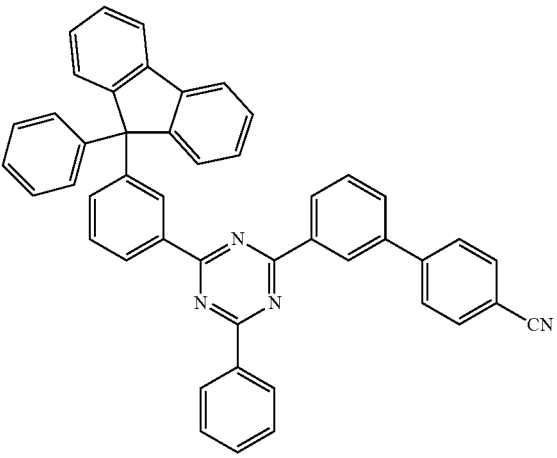 [SMILES: N#Cc1ccc(-c2cccc(-c3nc(-c4ccccc4)nc(-c4cccc(C5(c6ccccc6)c6ccccc6-c6ccccc65)c4)n3)c2)cc1]

Following the procedure described above using 2-chloro-4-phenyl-6-(3-(9-phenyl-9H-fluoren-9-yl)phenyl)-1,3,5-triazine (11.4 g, 22.5 mmol), 3'-(4,4,5,5-tetramethyl-1,3,2-dioxaborolan-2-yl)-[1,1'-biphenyl]-4-carbonitrile (7.2 g, 23.6 mmol), Pd(PPh$_3$)$_4$ (0.52 g, 0.45 mmol), K$_2$CO$_3$ (6.2 g, 44.9 mmol), deaerated THF/water (2:1, 110 mL) and 18 h reaction time, 5.8 g (40%) of a white solid were obtained after trituration with toluene and precipitation from toluene/n-hexane instead of column chromatography. Final purification was achieved by sublimation. m/z=651 ([M+H]$^+$).

4'-(4-phenyl-6-(3-(9-phenyl-9H-fluoren-9-yl)phenyl)-1,3,5-triazin-2-yl)-[1,1'-biphenyl]-4-carbonitrile A flask was flushed with nitrogen and charged with 2-chloro-4-phenyl-6-(3-(9-phenyl-9H-fluoren-9-yl)phenyl)-1,3,5-triazine (10 g, 19.7 mmol), 4'-(4,4,5,5-tetramethyl-1,3,2-dioxaborolan-2-yl)-[1,1'-biphenyl]-4-carbonitrile (6.6 g, 21.7 mmol), Pd(PPh$_3$)$_4$ (0.46 g, 0.39 mmol), and K$_2$CO$_3$ (5.4 g, 39.4 mmol). A mixture of deaerated THF/water (13:1, 270 mL) was added and the reaction mixture was heated to reflux under a nitrogen atmosphere for 16 h. After cooling down to room temperature, the THF was removed in vacuo, dichloromethane was added and the organic phase was washed with water three times. Subsequently, the organic phase was dried over Na$_2$SO$_4$ and filtered over a pad of silica. After rinsing with additional dichloromethane, the colorless filtrate was concentrated and n-hexane was added. After stirring for 1 h, the precipitate was collected by suction filtration and washed with n-hexane to yield 12.1 g (94%) of a white solid after drying. Final purification was achieved by sublimation. m/z=651 ([M+H]$^+$).

Synthesis of Compounds of Formula 1 with Ar$^2$=C$_6$H$_5$CN:

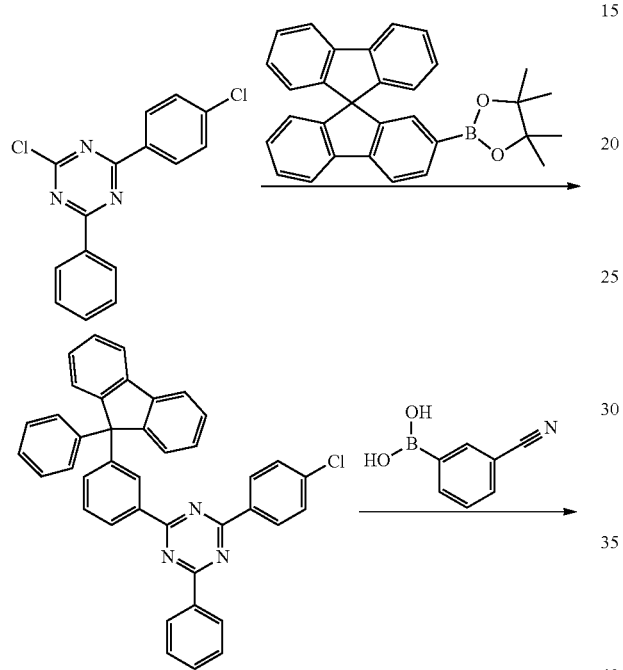

2-(4-chlorophenyl)-4-phenyl-6-(3-(9-phenyl-9H-fluoren-9-yl)phenyl)-1,3,5-triazine

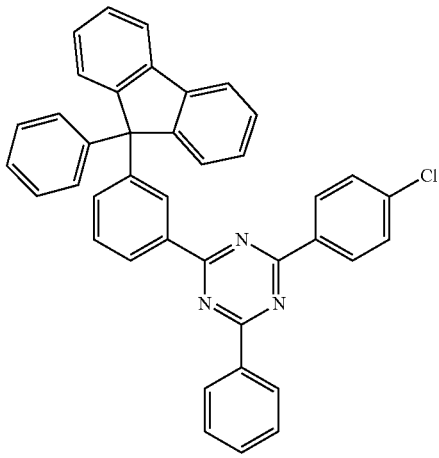 [SMILES: Clc1ccc(-c2nc(-c3ccccc3)nc(-c3cccc(C4(c5ccccc5)c5ccccc5-c5ccccc54)c3)n2)cc1]

A flask was flushed with nitrogen and charged with 2-chloro-4-(4-chlorophenyl)-6-phenyl-1,3,5-triazine (9.8 g, 32.3 mmol), 4,4,5,5-tetramethyl-2-(3-(9-phenyl-9H-fluoren-9-yl)phenyl)-1,3,2-dioxaborolane (15.1 g, 33.9 mmol), Pd(PPh$_3$)$_4$ (0.75 g, 0.65 mmol), and K$_2$CO$_3$ (8.9 g, 64.6 mmol). A mixture of deaerated THF/water (2:1, 160 mL) was added and the reaction mixture was heated to reflux under a nitrogen atmosphere for 70 h. After cooling down to room temperature, the THF was removed in vacuo, dichloromethane was added and the organic phase was washed with water three times. Subsequently, the organic phase was dried over MgSO$_4$ and filtered over a pad of Florisil. After rinsing with additional dichloromethane, the filtrate was evaporated to dryness and the resulting solid was triturated with n-hexane. Further purification was achieved by column chromatography (silica, n-hexane/dichloromethane 8:2) to yield 14.4 g (76%) of a white solid after drying.

4'-(4-phenyl-6-(3-(9-phenyl-9H-fluoren-9-yl)phenyl)-1,3,5-triazin-2-yl)-[1,1'-biphenyl]-3-carbonitrile

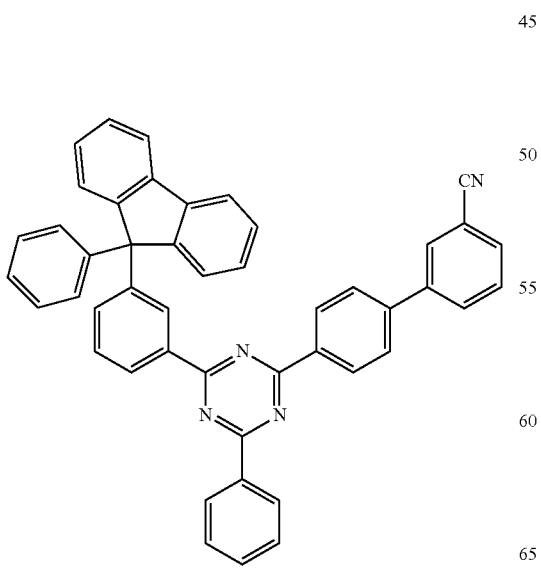

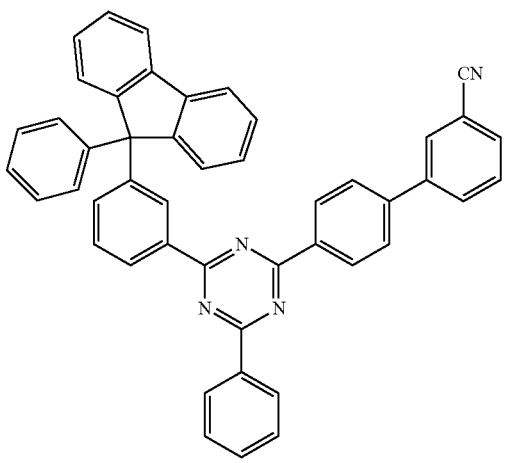 [SMILES: N#Cc1cccc(-c2ccc(-c3nc(-c4ccccc4)nc(-c4cccc(C5(c6ccccc6)c6ccccc6-c6ccccc65)c4)n3)cc2)c1]

A flask was flushed with nitrogen and charged with 2-(4-chlorophenyl)-4-phenyl-6-(3-(9-phenyl-9H-fluoren-9- yl)phenyl)-1,3,5-triazine (7 g, 12 mmol), (3-cyanophenyl) boronic acid (2.1 g, 14.4 mmol), chloro(crotyl)(2-dicyclohexylphosphino-2',6'-dimethoxybiphenyl)palladium(II) (0.15 g, 0.24 mmol), and $K_3PO_4$ (5.08 g, 24 mmol). A mixture of deaerated THF/water (4:1, 130 mL) was added and the reaction mixture was heated to 50 C.° under a nitrogen atmosphere for 20.5 h. After cooling down to room temperature, the THF was removed in vacuo, dichloromethane was added and the organic phase was washed with water three times. Subsequently, the organic phase was dried over $MgSO_4$ and filtered over a pad of silica and Florisil. After rinsing with additional dichloromethane, the filtrate was concentrated and n-hexane was added to complete the precipitation. The resulting solid was collected by suction filtration and washed with n-hexane. Further purification was achieved by repeated trituration with hot ethyl acetate to yield 6.5 g (83%) of a white solid after drying. Final purification was achieved by sublimation. m/z=651 ([M+H]$^+$).

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a <1 mm hole is pierced into the lid).

Reduction Potential

The reduction potential is determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc$^+$/Fc redox couple, afforded finally the values reported above. All studied compounds as well as the reported comparative compounds showed well-defined reversible electrochemical behaviour.

General Procedure for Fabrication of OLEDs

For top emission devices, Examples 1 to 8 and comparative example 1, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes. 100 nm Ag were deposited on the substrate at a pressure of $10^{-5}$ to $10^{-7}$ mbar to form the anode.

Then, 92 vol.-% Biphenyl-4-yl(9,9-diphenyl-9H-fluoren-2-yl)-[4-(9-phenyl-9H-carbazol-3-yl)phenyl]-amine (CAS 1242056-42-3) with 8 vol.-% 2,2',2"-(cyclopropane-1,2,3-triylidene)tris(2-(p-cyanotetrafluorophenyl)acetonitrile) was vacuum deposited on the anode, to form a HIL having a thickness of 10 nm. Then, Biphenyl-4-yl(9,9-diphenyl-9H-fluoren-2-yl)-[4-(9-phenyl-9H-carbazol-3-yl)phenyl]-amine was vacuum deposited on the HIL, to form a HTL having a thickness of 118 nm.

Then N,N-bis(4-(dibenzo[b,d]furan-4-yl)phenyl)-[1,1':4',1"-terphenyl]-4-amine (CAS 1198399-61-9) was vacuum deposited on the HTL, to form an electron blocking layer (EBL) having a thickness of 5 nm.

Then 97 vol.-% H09 (Sun Fine Chemicals) as EML host and 3 vol.-% BD200 (Sun Fine Chemicals) as fluorescent blue dopant were deposited on the EBL, to form a blue-emitting EML with a thickness of 20 nm.

Then the hole blocking layer is formed with a thickness of 5 nm by depositing 2,4-diphenyl-6-(4',5',6'-triphenyl-[1,1':2',1":3",1'":3'",1""-quinquephenyl]-3""-yl)-1,3,5-triazine on the emission layer.

Then, the electron transporting layer is formed on the hole blocking layer according to Examples 1 to 8 and comparative example 1 with a the thickness of 31 nm. The electron transport layer comprises 50 wt.-% matrix compound and 50 wt.-% of alkali organic complex. The composition is shown in Table 2.

Then the electron injection layer is formed on the electron transporting layer by deposing Yb with a thickness of 2 nm. Ag is evaporated at a rate of 0.01 to 1 Å/s at $10^{-7}$ mbar to form a cathode with a thickness of 11 nm.

A cap layer of Biphenyl-4-yl(9,9-diphenyl-9H-fluoren-2-yl)-[4-(9-phenyl-9H-carbazol-3-yl)phenyl]-amine is formed on the cathode with a thickness of 75 nm.

The OLED stack is protected from ambient conditions by encapsulation of the device with a glass slide. Thereby, a cavity is formed, which includes a getter material for further protection.

To assess the performance of the inventive examples compared to the prior art, the current efficiency is measured under ambient conditions (20° C.). Current voltage measurements are performed using a Keithley 2400 sourcemeter, and recorded in V. At 10 mA/cm$^2$ for top emission devices, a calibrated spectrometer CAS140 from Instrument Systems is used for measurement of CIE coordinates and brightness in Candela. Lifetime LT of the device is measured at ambient conditions (20° C.) and 30 mA/cm$^2$, using a Keithley 2400 sourcemeter, and recorded in hours.

The brightness of the device is measured using a calibrated photo diode. The lifetime LT is defined as the time till the brightness of the device is reduced to 97% of its initial value.

The light output in external efficiency EQE and power efficiency (lm/W efficiency) are determined at 10 mA/cm$^2$ for top emission devices.

To determine the efficiency EQE in % the light output of the device is measured using a calibrated photodiode.

To determine the power efficiency in lm/W, in a first step the luminance in candela per square meter (cd/m2) is measured with an array spectrometer CAS140 CT from Instrument Systems which has been calibrated by Deutsche Akkreditierungsstelle (DAkkS). In a second step, the luminance is then multiplied by π and divided by the voltage and current density.

In bottom emission devices, the emission is predominately Lambertian and quantified in percent external quantum efficiency (EQE) and power efficiency in lm/W.

In top emission devices, the emission is forward directed, non-Lambertian and also highly dependent on the microcavity. Therefore, the external quantum efficiency (EQE) and power efficiency in lm/W will be higher compared to bottom emission devices.

Technical Effect of the Invention

As can be seen in Table 1, the mp, Tg and reduction potential, calculated HOMO and calculated dipole moment of compounds of formula 1 are in a range suitable for use in organic electronic devices.

Top Emission Devices

In Table 2 is shown the performance of in organic electronic device comprising an organic semiconductor layer comprising a compound of formula 1 and an alkali organic complex.

In comparative example 1, compound ETM-1 was used as matrix compound:

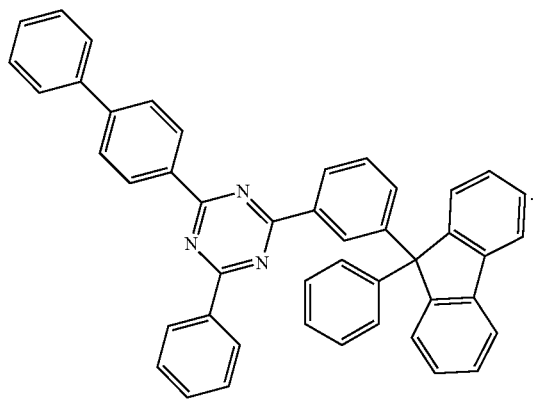

ETM-1

The dipole moment of ETM-1 is 0.51 Debye and the calculated HOMO level is −5.80 eV.

The organic semiconductor layer comprises 50 vol.-% ETM-1 and 50 vol.-% LiQ. The operating voltage is 3.5 V and the cd/A efficiency is 7.5 cd/A. The lifetime is 41 hours.

In Example 1, the organic semiconductor layer comprises 50 vol.-% compound of formula 1 F9 and 50 vol.-% LiQ. The operating voltage is 3.6 V. The cd/A efficiency is improved to 8 cd/A and the lifetime is improved to 51 hours.

In Example 2 and 3, the organic semiconductor layer comprises the same compound of formula 1 as in Example 1. In Example 2, Lithium tetra(1H-pyrazol-1-yl)borate LI-1 is used instead of LiQ. In Example 3, lithium 2-(diphenylphosphoryl)phenolate LI-2 is used instead of LiQ. The cd/A efficiency is high at 8 and 8.3 cd/A, respectively. The lifetime is long at 48 and 49 hours, respectively.

In Example 4, the organic semiconductor layer comprises compound of formula 1 F8 and alkali organic complex LiQ. The cd/A efficiency is high at 7.6 cd/A and the lifetime is further improved to 88 hours.

In Example 5, the organic semiconductor layer comprises compound of formula 1 F3 and alkali organic complex LiQ. The lifetime is further improved to 61 hours.

In Example 6, the organic semiconductor layer comprises the same compound of formula 1 as in Example 5. In Example 6, Lithium tetra(1H-pyrazol-1-yl)borate LI-1 is used instead of LiQ. The lifetime is long at 56 hours.

In Example 7, the organic semiconductor layer comprises compound of formula 1 F2 and alkali organic complex LiQ. The cd/A efficiency is high at 7.9 cd/A and the lifetime is long at 53 hours.

In Example 8, the organic semiconductor layer comprises the same compound of formula 1 as in Example 7. In Example 7, Lithium tetra(1H-pyrazol-1-yl)borate LI-1 is used instead of LiQ. The cd/A efficiency is high at 7.7 cd/A and the lifetime is long at 50 hours.

In summary, improved cd/A efficiency and/or improved lifetime may be achieved when the organic semiconductor layer comprises a compound of formula 1. High performance may be achieved for a wide range of alkali organic complexes.

TABLE 1

Properties of compound of formula 1

| Refered to as: | Structure | mp/° C. | Tg/° C. | Reduction potential/V | Calculated HOMO/eV | Dipole moment/Debye |
|---|---|---|---|---|---|---|
| F2 | 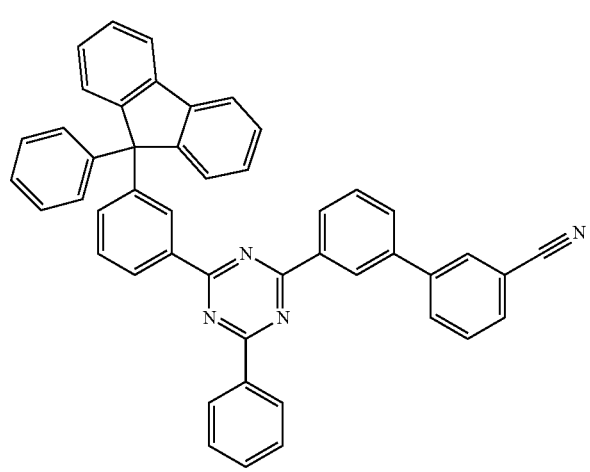 [SMILES: N#Cc1cccc(-c2cccc(-c3nc(-c4ccccc4)nc(-c4cccc(C5(c6ccccc6)c6ccccc6-c6ccccc65)c4)n3)c2)c1] | — | 111 | −2.18 | −5.82 | 4.31 |

TABLE 1-continued
| Refered to as: | Structure | mp/° C. | Tg/ ° C. | Reduction potential/V | Calculated HOMO/eV | Dipole moment/ Debye |
|---|---|---|---|---|---|---|
| F3 | 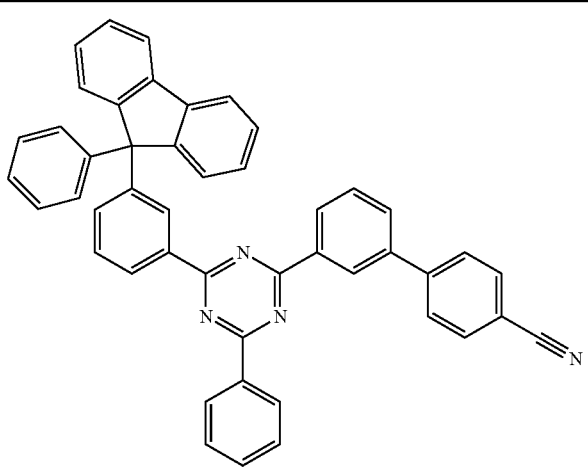 | — | — | −2.17 | −5.88 | 5.60 |
| F4 | 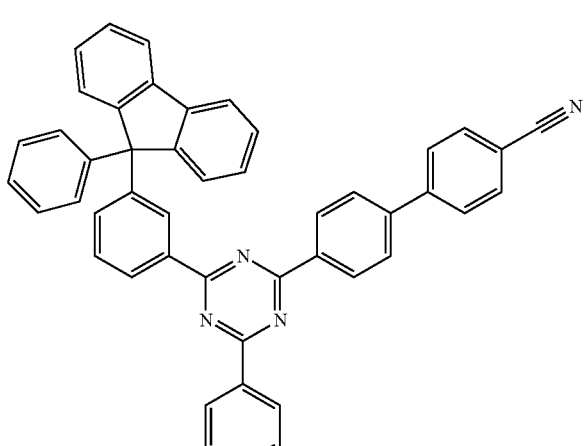 | — | 135 | −2.03 | −5.88 | 5.87 |
| F5 | 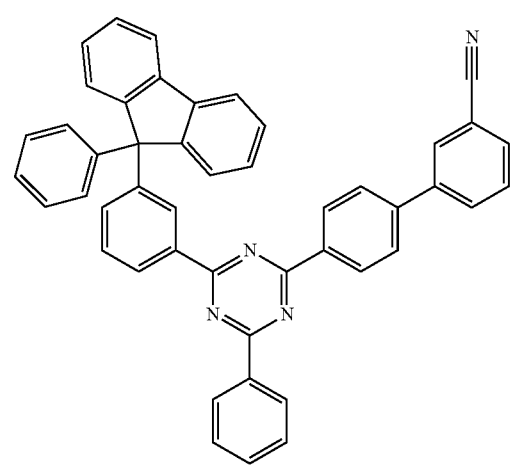 [SMILES: N#Cc1cccc(-c2ccc(-c3nc(-c4ccccc4)nc(-c4cccc(C5(c6ccccc6)c6ccccc6-c6ccccc65)c4)n3)cc2)c1] | 286 | 124 | | −5.96 | 5.03 |

TABLE 1-continued

Properties of compound of formula 1

| Refered to as: | Structure | mp/° C. | Tg/ ° C. | Reduction potential/V | Calculated HOMO/eV | Dipole moment/ Debye |
|---|---|---|---|---|---|---|
| F7 | 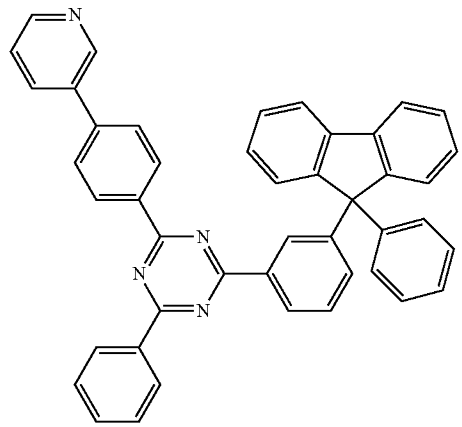 [SMILES: c1ccc(-c2nc(-c3ccc(-c4cccnc4)cc3)nc(-c3cccc(C4(c5ccccc5)c5ccccc5-c5ccccc54)c3)n2)cc1] | — | — | | −5.83 | 2.48 |
| F8 | 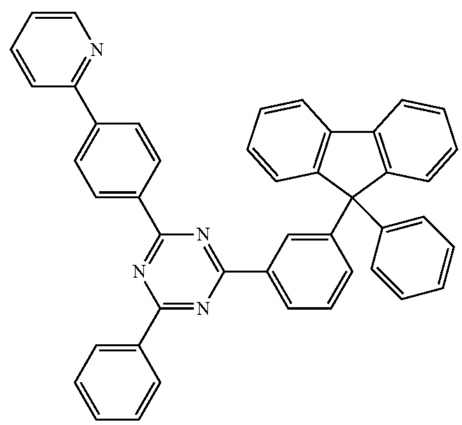 [SMILES: c1ccc(-c2nc(-c3ccc(-c4ccccn4)cc3)nc(-c3cccc(C4(c5ccccc5)c5ccccc5-c5ccccc54)c3)n2)cc1] | 267 | 123 | | −5.79 | 1.62 |
| F9 | 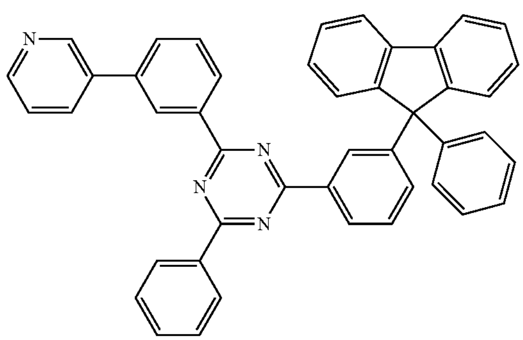 [SMILES: c1ccc(-c2nc(-c3cccc(-c4cccnc4)c3)nc(-c3cccc(C4(c5ccccc5)c5ccccc5-c5ccccc54)c3)n2)cc1] | 201 | 106 | −2.17 | −5.85 | 2.84 |

TABLE 2

Performance of an organic electroluminescent device comprising an organic semiconductor layer comprising a compound of formula 1 and an alkali organic complex

| | Matrix compound | Concentration of matrix compound (vol.-%) | Alkali organic complex | Concentration of alkali organic complex (vol.-%) | Thickness electron transport layer (nm) | Operating voltage at 10 mA/cm$^2$ (V) | cd/A efficiency at 10 mA/cm$^2$ (cd/A) | LT97 at 30 mA/cm$^2$ (h) |
|---|---|---|---|---|---|---|---|---|
| Comparative example 1 | ETM-1 | 50 | LiQ | 50 | 31 | 3.5 | 7.5 | 41 |
| Example 1 | F9 | 50 | LiQ | 50 | 31 | 3.6 | 8.0 | 51 |

TABLE 2-continued

Performance of an organic electroluminescent device comprising an organic semiconductor layer comprising a compound of formula 1 and an alkali organic complex

| | Matrix compound | Concentration of matrix compound (vol.-%) | Alkali organic complex | Concentration of alkali organic complex (vol.-%) | Thickness electron transport layer (nm) | Operating voltage at 10 mA/cm$^2$ (V) | cd/A efficiency at 10 mA/cm$^2$ (cd/A) | LT97 at 30 mA/cm$^2$ (h) |
|---|---|---|---|---|---|---|---|---|
| Example 2 | F9 | 70 | LI-1 | 30 | 31 | 3.8 | 8.0 | 48 |
| Example 3 | F9 | 50 | LI-2 | 50 | 31 | 3.7 | 8.3 | 49 |
| Example 4 | F8 | 50 | LiQ | 50 | 31 | 3.8 | 7.6 | 88 |
| Example 5 | F3 | 50 | LiQ | 50 | 31 | 3.6 | 7.3 | 61 |
| Example 6 | F3 | 70 | LI-1 | 30 | 31 | 3.8 | 7.1 | 56 |
| Example 7 | F2 | 50 | LiQ | 50 | 31 | 3.6 | 7.9 | 53 |
| Example 8 | F2 | 50 | LI-1 | 50 | 31 | 3.7 | 7.7 | 50 |

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound of formula 1,

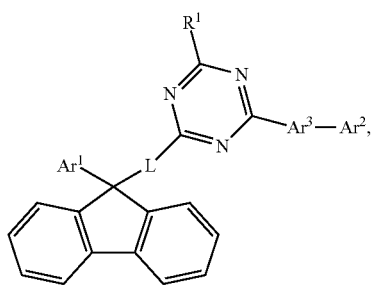

(1)

wherein

R$^1$ is selected from a C$_1$ to C$_{16}$ alkyl group, substituted or unsubstituted C$_6$ to C$_{24}$ aryl group, or a substituted or unsubstituted C$_2$ to C$_{24}$ heteroaryl group, wherein the substituent of the substituted C$_6$ to C$_{24}$ aryl group and of the substituted C$_2$ to C$_{24}$ heteroaryl group is selected from C$_1$ to C$_{16}$ alkyl, C$_1$ to C$_{16}$ alkoxy, partially or perfluorinated C$_1$ to C$_{16}$ alkyl, partially or perfluorinated C$_1$ to C$_{16}$ alkoxy, F, CN, C$_6$ to C$_{18}$ aryl or C$_3$ to C$_{25}$ heteroaryl;

L is selected from an unsubstituted or substituted C$_6$ to C$_{24}$ arylene group, wherein the substituents of the substituted C$_6$ to C$_{24}$ arylene group are selected from C$_1$ to C$_{16}$ alkyl or C$_6$ to C$_{12}$ aryl;

Ar$^1$ is selected from an unsubstituted C$_6$ to C$_{18}$ aryl group;

Ar$^2$ is selected from the group consisting of —C$_6$H$_5$CN or C$_2$ to C$_9$ heteroaryl containing N;

Ar$^3$ is an unsubstituted C$_6$ arylene.

2. The compound of formula 1 according to claim 1, wherein

R$^1$ is selected from a C$_1$ to C$_{12}$ alkyl group or unsubstituted C$_6$ to C$_{12}$ aryl group;

L is selected from an unsubstituted C$_6$ to C$_{12}$ arylene group;

Ar$^1$ is selected from C$_6$ to C$_{18}$ aryl;

Ar$^3$ is an unsubstituted C$_6$ arylene; and

Ar$^2$ is selected from the group consisting of —C$_6$H$_5$CN or C$_2$ to C$_9$ N-containing heteroaryl.

3. The compound of formula 1 according to claim 1, wherein

R$^1$ is independently selected from B1 to B16, B17 to B20 and B21 to B25, wherein B1 to B11 are unsubstituted aryl groups and B12 to B16 are substituted aryl groups:

(B1)

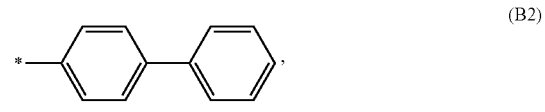

(B2)

(B3)

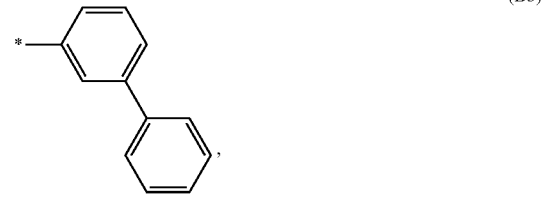

(B4)

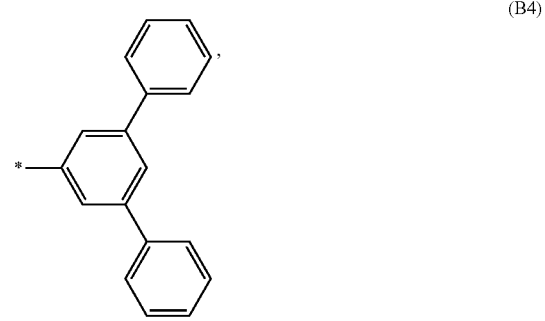

(B5)

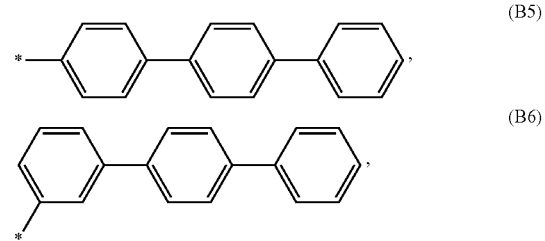

(B6)

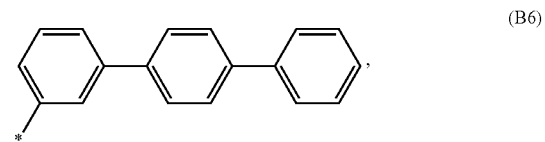

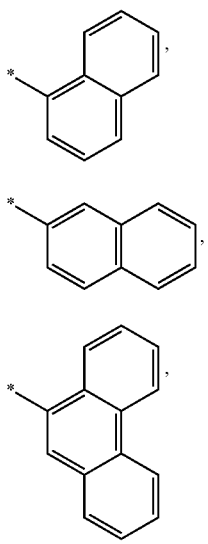
(B7) 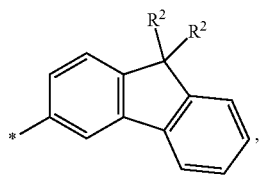
(B8)
(B9)
(B15) 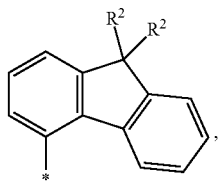
(B16)
and
wherein $R^2$ is independently selected from H, $C_1$ to $C_{16}$ alkyl, $C_6$ to $C_{18}$ aryl and $C_3$ to $C_{25}$ heteroaryl;
wherein B17 to B20 are unsubstituted dibenzofuranyl groups:
(B10)
(B11)
(B12)
(B13)
(B14)
(B17) 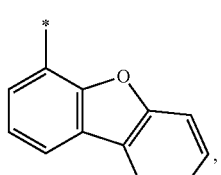
(B18) 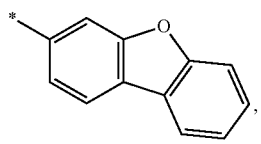
(B19) 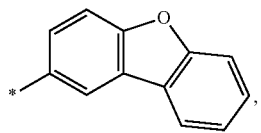
(B20) 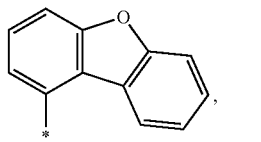
wherein B21 to B25 are unsubstituted dibenzothiophenyl groups:
(B21) 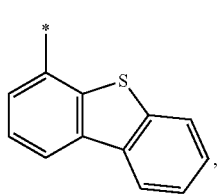

-continued
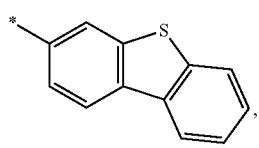
(B22)
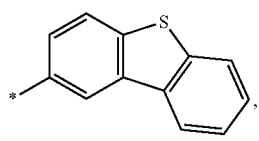
(B24)
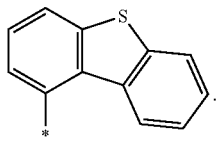
(B25)
4. The compound of formula 1 according to claim 1, wherein $Ar^1$ is independently selected from B1 to B9:
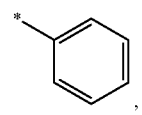
(B1)
(B2)
(B3)
(B4)
(B5)
(B6)
-continued
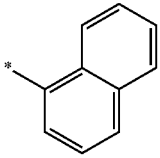
(B7)
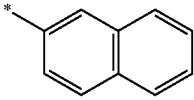
(B8)
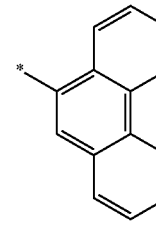
(B9)
5. The compound of formula 1 according to claim 1, wherein
$Ar^3$ is selected from C1 and C2:
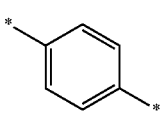
(C1)
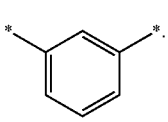
(C2)
6. The compound of formula 1 according to claim 1, wherein
L is selected from C1 to C13:
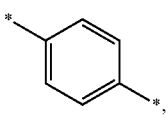
(C1)
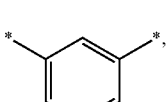
(C2)
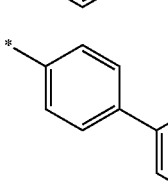
(C3)

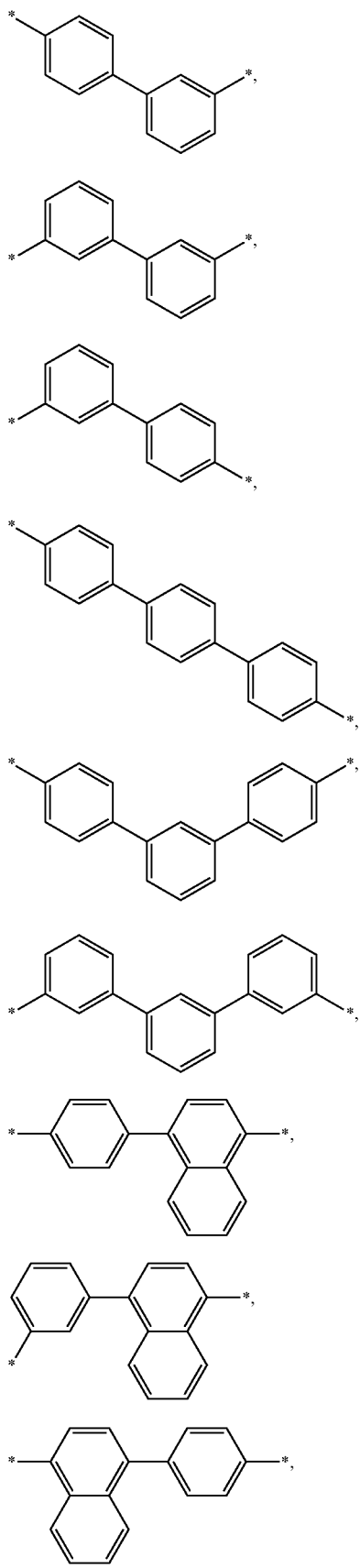
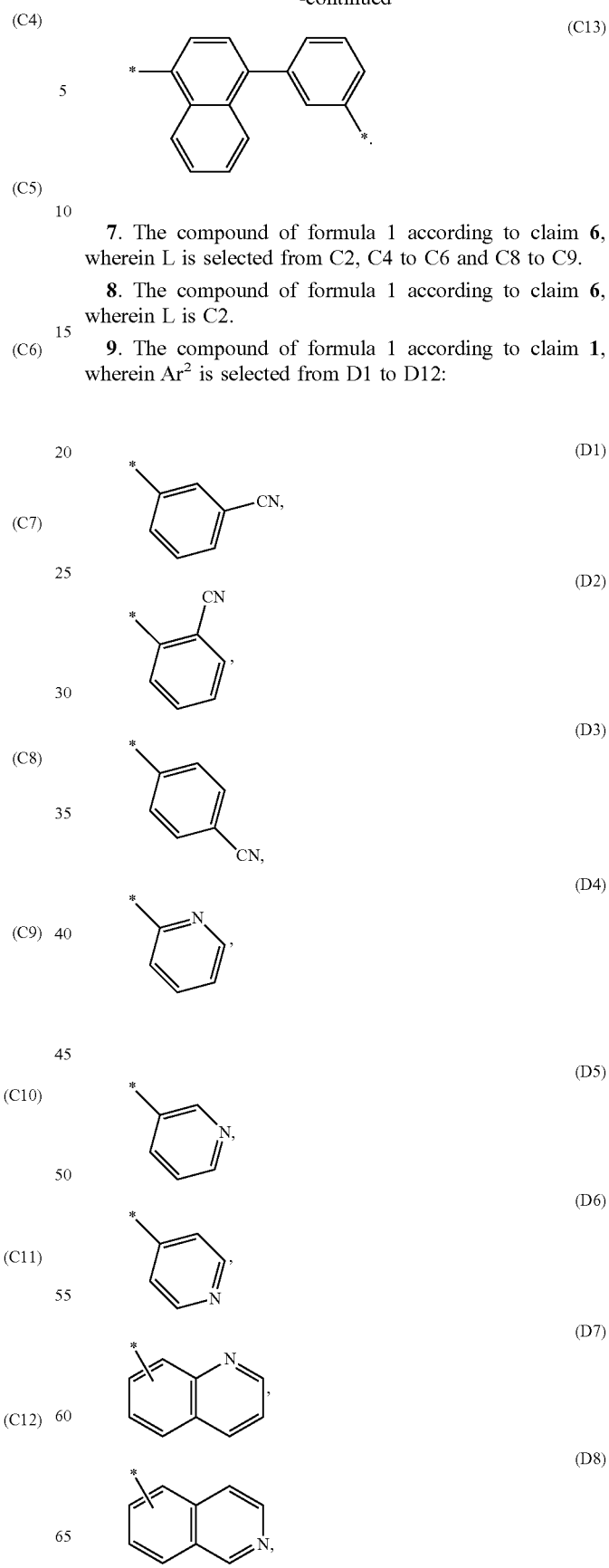
7. The compound of formula 1 according to claim 6, wherein L is selected from C2, C4 to C6 and C8 to C9.
8. The compound of formula 1 according to claim 6, wherein L is C2.
9. The compound of formula 1 according to claim 1, wherein $Ar^2$ is selected from D1 to D12:

-continued
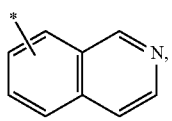 (D9)
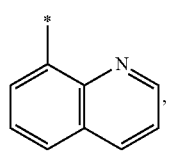 (D10)
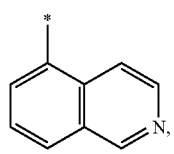 (D11)
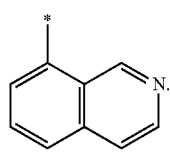 (D12)
10. The compound of formula 1 according to claim 1, wherein the compound of formula 1 is selected from F1 to F11:
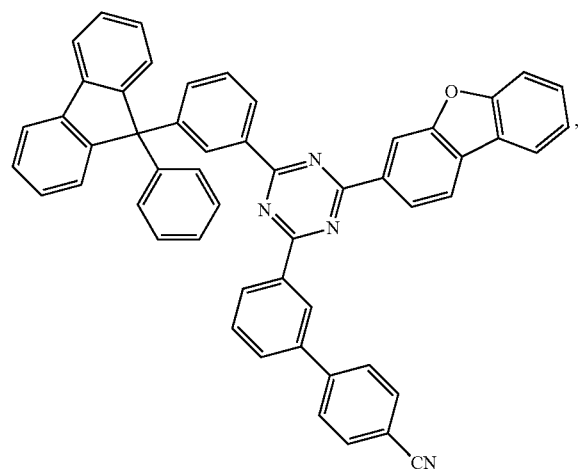 (F1)
-continued
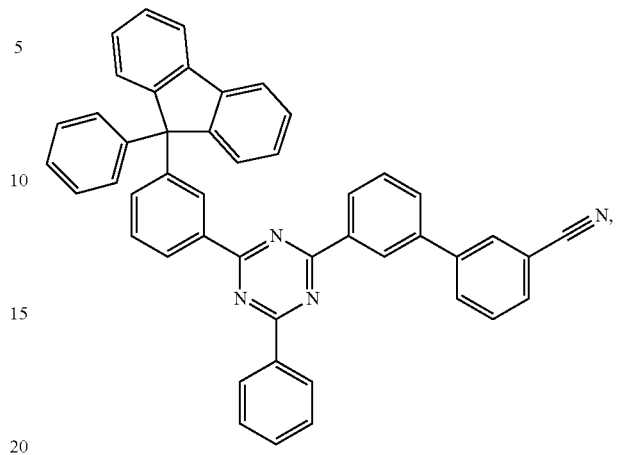 (F2)
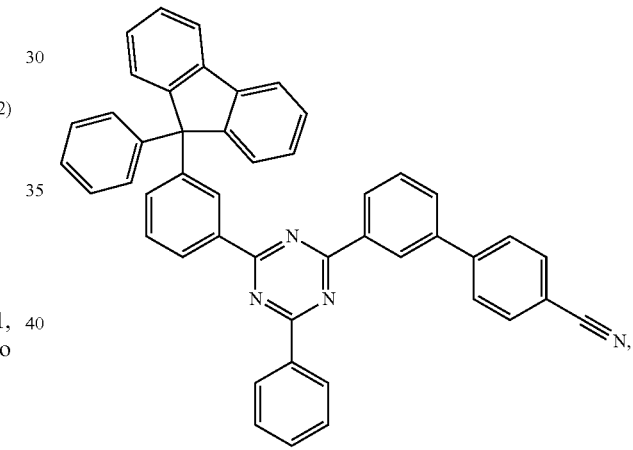 (F3)
(F4)

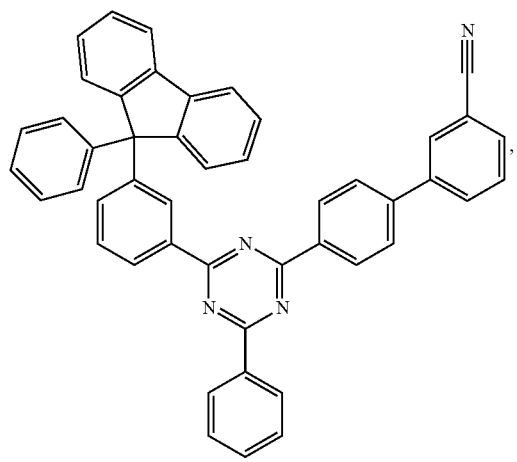
(F5)
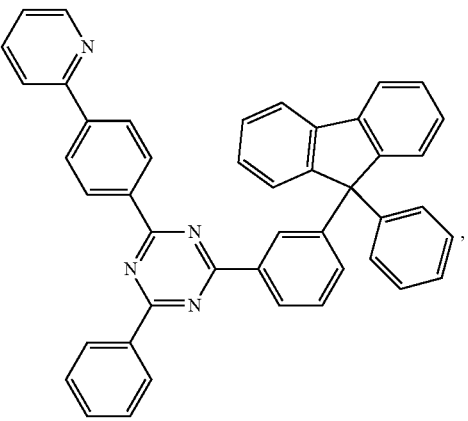
(F8)
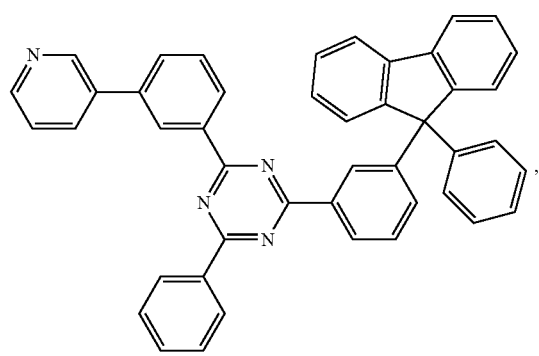
(F6)
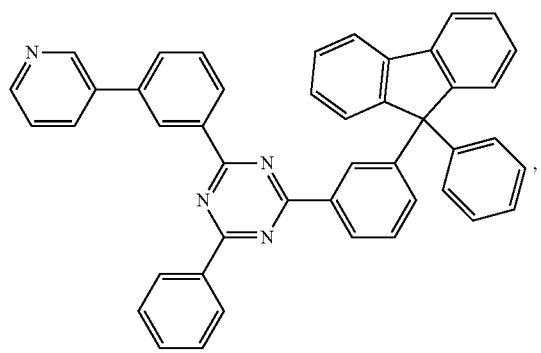
(F9)
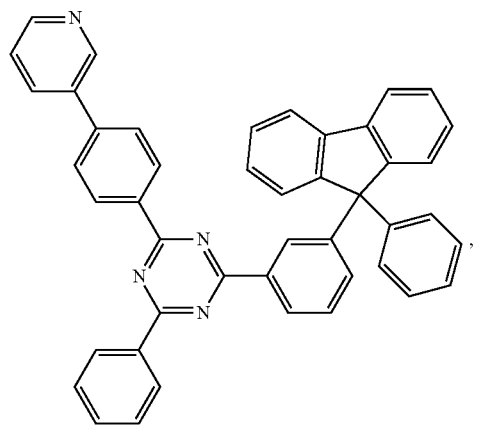
(F7)
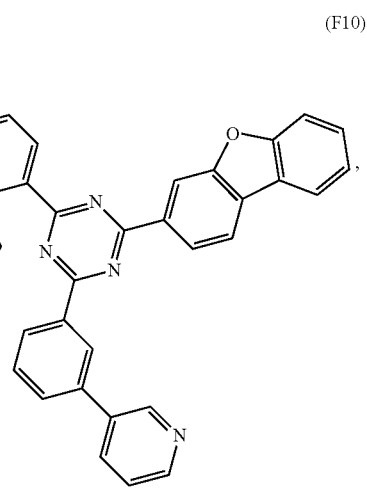
(F10)

-continued

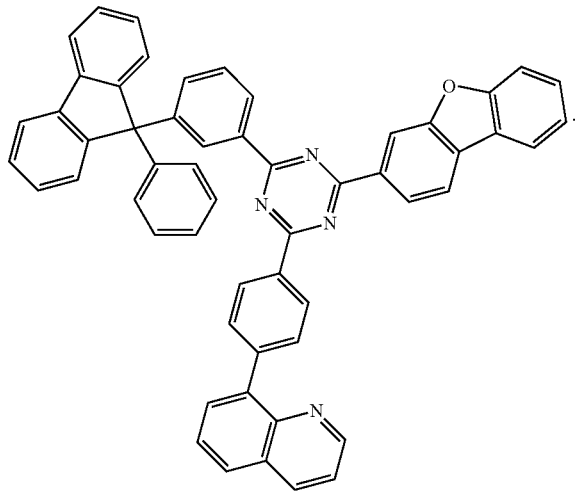

(F11)

11. An organic semiconductor layer comprising at least one compound of formula 1 according to claim 1.

12. The organic semiconductor layer according to claim 11, further comprising a metal, metal salt or organic alkali metal complex.

13. An organic electronic device comprising an organic semiconductor layer according to claim 11.

14. The organic electronic device according to claim 13, wherein the organic electronic device comprises at least one organic semiconductor layer that comprises at least one alkali halide or alkali organic complex.

15. The organic electronic device according to claim 13, wherein the electronic device is a light emitting device, thin film transistor, a battery, a display device or a photovoltaic cell.

16. The organic electronic device according to claim 15, wherein the electronic device is a light emitting device.

* * * * *